United States Patent [19]

Hesse et al.

[11] Patent Number: 6,013,814
[45] Date of Patent: Jan. 11, 2000

[54] VITAMIN D ANALOGUES

[75] Inventors: Robert Henry Hesse, Winchester; Sundara Katugam Srinivasasetty Setty, Cambridge; Malathi Ramgopal, Andover; Gaddam Subba Reddy, Lexington, all of Mass.

[73] Assignee: Research Institute for Medicine and Chemistry, Inc., Cambridge, Mass.

[21] Appl. No.: 09/175,311

[22] Filed: Oct. 20, 1998

Related U.S. Application Data

[62] Division of application No. 08/537,869, filed as application No. PCT/GB94/01587, Jul. 22, 1994, Pat. No. 5,872,140.

[30] Foreign Application Priority Data

Jul. 23, 1993 [GB] United Kingdom .................. 9315253

[51] Int. Cl.⁷ ..................... C07C 401/00; C07D 249/04; A61K 31/41; A61K 31/655
[52] U.S. Cl. ................... 552/10; 552/4; 514/63; 514/151; 514/236.2; 514/319; 514/359; 544/132; 546/14; 546/205; 548/255
[58] Field of Search ......................... 552/10, 4; 514/151, 514/63, 236.2, 319, 359; 544/132; 546/14, 205; 548/255

[56] References Cited

U.S. PATENT DOCUMENTS

| 4,772,433 | 9/1988 | Hesse | 260/397.2 |
| 5,446,635 | 8/1995 | Herf et al. | 514/167 |

FOREIGN PATENT DOCUMENTS

| 2 114 570 | 8/1983 | United Kingdom . |
| 2 114 570 | 8/1993 | United Kingdom . |
| WO 94/07853 | 4/1994 | WIPO . |
| WO-A1-94 07853 | 4/1994 | WIPO . |

OTHER PUBLICATIONS

Rahul et al., Chemical Abstracts, vol. 103, No. 19, abstract No. 160 275s, Nov. 1985.

Perlman et al., 1–alpha–Hydroxy–19–Nor–Vitamin D C–22 Aldehyde. A Valuable Intermediate in the Synthesis of side Chain Modified 1–alpha,25–Dihydroxy–19–Nor–Vitamine D3, Tetrahedron Letters, vol. 33, No. 21, pp. 2937–2940, May 1992.

Calverley, Synthesis of MC 903, A Biologically Active Vitamin D Metabolite Analogue, Tetrahedron Letters, vol. 43, No. 17, pp. 4609–4619, 1987.

Cram and Hammond, "Organic Chemistry", McGraw-Hill Book Co., NY, 2nd Ed pp. 565–567, 1964.

*Primary Examiner*—Mukund J. Shah
*Assistant Examiner*—Brenda Coleman
*Attorney, Agent, or Firm*—Bacon & Thomas

[57] ABSTRACT

The present invention relates to novel 1α-hydroxy vitamin D derivatives in which the 17-position side chain carries an azide or optionally substituted 1,2,3-triazole group, including compounds of general formula (I) where $R^1$ represents a methyl group having α- or β-configuration; W represents a valence bond or a $C_{1-5}$ alkylene group; X represents azide or an optionally substituted triazole group; and A= represents a cyclohexylidene moiety characteristic of the A-ring of a 1α-hydroxylated vitamin D or analogue thereof. Active compounds of the invention exhibit cell modulating activity while exhibiting a substantial lack of calcaemic effect.

8 Claims, No Drawings

VITAMIN D ANALOGUES

This application is a divisional application of U.S. application Ser. No. 08/537,869 filed Mar. 21, 1996, U.S. Pat. No. 5,872,140 which is a 371 of PCT/GB94/01587 filed Jul. 22, 1994.

This invention relates to novel vitamin D analogues, more particularly to 1α-hydroxy vitamin $D_3$ analogues having a modified side chain at the 17-position and exhibiting cell modulating activity.

Vitamin $D_3$, which has the formula

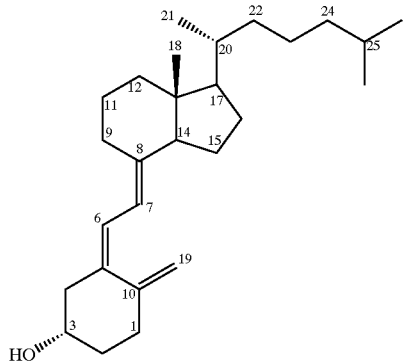

is well known to play a vital role in the metabolism of calcium, by promoting intestinal absorption of calcium and phosphorus, maintaining adequate serum levels of calcium and phosphorus and stimulating mobilisation of calcium from the bone fluid compartment in the presence of parathyroid hormone.

About 20 years ago it was learned that the D vitamins undergo hydroxylation in vivo, hydroxylation at the 25-position occurring in the liver and hydroxylation at the 1α-position occurring in the kidney, the resulting 1α,25-dihydroxy metabolite being the biologically active material. This discovery led to the synthesis of many analogues of vitamin D, evaluation of which indicated that hydroxyl groups at the 1α-position and at either the 24R- or the 25-position were essential for a compound or metabolite thereof to exhibit a substantial effect on calcium metabolism. While, as indicated above, such hydroxyl groups will normally ultimately be introduced in vivo, hydroxylation at the 24R- or 25-position occurring rather more readily than at the 1α-position, the use of vitamin D analogues already so hydroxylated has proved of substantial advantage by virtue of their enhanced levels of activity and their rapidity of action and subsequent elimination from the body. It will be appreciated that 1α-hydroxylated vitamin D derivatives are of especial benefit to patients suffering from renal failure.

Examples of hydroxylated vitamin D analogues in current use include the natural metabolite 1α,25-dihydroxy vitamin $D_3$ and 1α-hydroxy vitamin $D_3$ (which is readily 25-hydroxylated in vivo). Other reportedly promising compounds include 1α,24R-dihydroxy vitamin $D_3$, $D_2$ analogues of the above compounds and 1α,25-dihydroxy analogues carrying fluorine atoms at the 24-, 26- and/or 27-positions (see De Luca and Schnoes, *Ann. Rev. Biochem.* (1983), 52, pp 411–439 and De Luca et al., *Top, Curr. Chem.* (1979), 83, pp 1–65).

More recently it has been learned that the natural metabolite 1α,25-dihydroxy vitamin $D_3$ has additional effects on cellular metabolism. These cell modulating effects include stimulation of cell maturation and differentiation (Tanaka et al., *Biochem. J.* (1982), 204, pp 713–719; Amento et al., *J. Clin. Invest.* (1984), 73, pp 731–739; Colston et al., *Endocrinology* (1981), 108, pp 1083–1086; Abe et al., *Proc. Nat. Acad. Sci.* (1981), 78, pp 4990–4994) and immunosuppressive effects (e.g. inhibition of interleukin II production) (Rigby, *Immunology Today* (1988), 9, pp 54–58).

Still more recently, an immunopotentiating effect of 1α,25-dihydroxy vitamin $D_3$ has been observed, the compound having been found to stimulate the production of bactericidal oxygen metabolites and the chemotactic response of leukocytes (see, for example, Cohen et al., *J. Immunol.* (1986), 136, pp 1049–1053). It is well known that leukocytes play a major role in the body's defence against various infections (see, for example, Roitt, Brostoff and Male, "Immunology" $2_{nd}$ Ed. (1989), C. V. Mosby, St. Louis, sec 16.10–16.13 and 17.4–17.5), e.g. by adhering to and engulfing invading organisms (chemotactic response) and/or by producing superoxides and/or other toxic oxygen metabolites. It is known that this response may also be stimulated by mitogens such as the co-carcinogenic phorbal esters and γ-interferon, which are structurally quite different from vitamin D analogues.

By virtue of these effects on cellular metabolism, 1α,25-dihydroxy vitamin $D_3$ in principle has therapeutic potential in such diverse areas as treatment of psoriasis, inflammatory and autoimmune diseases, neoplasias and hyperplasias, as an adjunct in the chemotherapy of infections (inter alia bacterial, viral and fungal), and in other therapeutic modalities in which mononuclear phagocytes are involved. 1α,25-dihydroxy vitamin $D_3$ and 1α-hydroxy vitamin $D_3$ have also been proposed for use in the treatment of hypertension (Lind et al., *Acta Med. Scand.* (1987), 222, pp 423–427) and diabetes mellitus (Inomata et al., *Bone Mineral* (1986), 1, pp 187–192). Furthermore it has been suggested that 1α,25-dihydroxy vitamin $D_3$ may promote hair growth (*Lancet, Mar.* 4, 1989, p 478), may be useful in the treatment of acne (Malloy et al., Tricontinental Meeting for Investigative Dermatology, Washington, 1989), and may promote formation of nerve growth factor and improve cognition in elderly patients and in animal models of senile dementia. Vitamin D analogues exhibiting anti-progesterone activity, inhibition of blood clotting and fibrinolytic activity have also been reported.

The potent effects of 1α,25-dihydroxy vitamin $D_3$ and 1α-hydroxy vitamin $D_3$ on calcium metabolism will, however, normally preclude such uses, since dosages at a level sufficient to elicit e.g. a desired cell modulating, immunosuppressive or immunopotentiating effect tend to lead to unacceptable hypercalcaemia. This has led to attempts to synthesize new analogues having reduced effects on calcium metabolism but which still exhibit the desired effects on cellular metabolism etc.

There have been reports of new analogues which exhibit, to at least a moderate degree, this desired separation of activity. Thus the compound MC-903 (calcipotriol), which is a 22,23-unsaturated 1α,24R-dihydroxy vitamin $D_3$ analogue carrying a cyclopropyl group at the 24-position instead of the usual $C_{25}$–$C_{27}$ configuration of the cholestane side chain, and which is now used for the treatment of psoriasis, is reported to exhibit an effect on cell maturation comparable in magnitude to 1α,25-dihydroxy vitamin $D_3$, while exhibiting a smaller hypercalcaemic effect (Calverley, *Tetrahedron* (1987), 43, pp 4609–4619; and Holick, *Arch. Dermatol.* (1989), 125, pp 1692–1696). Similar claims have been made for analogues of 1α,25-dihydroxy vitamin $D_3$, e.g. the 22-oxa (Abe et al., *Endocrinology* (1989), 124; pp 2645–2647), the 24- and the 26- homo (Ostrem et al., *J Biol. Chem.* (1987), 262, pp 14164–14171), the 16-dehydro-23, 24-ethynyl (Zhou et al., Blood (1989), 74, pp 82–93) and the 19-nor-10-dihydro (Perlman et al., *Tetrahedron Lett.* (1990), pp 1823–1824).

Other analogues of 1α,25-dihydroxy vitamin $D_3$ which have been studied with the aim of achieving enhanced separation of differentiation-inducing activity and hypercalcaemic effect include 23-oxa, 23-thia and 23-aza derivatives (Kubodera et al., *Chem. Pharm. Bull.* (1991), 39, pp 3221–3224), 22-oxa analogues bearing side chains of different sizes (Kubodera et al., *Chem. Pharm. Bull.* (1992), 40, pp 1494–1499). and 20-epi analogues (Binderup et al., *Biochemical Pharmacology* (1991), 42, pp 1569–1575).

It does not appear possible to deduce from these disclosures either which compounds will exhibit cell modulating activity(or the level of any such activity) or to determine factors which lead to a separation of activities as regards cell modulation and calcium metabolism. Thus, for example, it has been observed that there are no strict relationships between differentiation-inducing activity and side chain length or hydrophilicity.

The majority of results suggest that the presence of a hydroxyl group towards the end of a cholestane-type side chain or homologue thereof is necessary for compounds to show significant cell modulating activity. However, the findings of Ostrem et al. (op. cit.) indicate that analogues having only a short, unsubstituted 17-position side chain (e.g. isopropyl or sec-butyl, as in homo- or bis-homopregnanes) exhibit quite substantial differentiation-inducing activity and are more potent than corresponding short side chain compounds bearing a side chain hydroxyl group.

A number of the proposed analogues appear to show cell modulating activity at a similar level to that of 1α,25-dihydroxy vitamin $D_3$, but also appear still to show appreciable effects on calcium metabolism, such activity being attenuated by at most two orders of magnitude relative to that of 1α,25-dihydroxy vitamin $D_3$. Moreover, it now appears in the case of many, if not all, of the new analogues described above as exhibiting separation of calcium and cellular metabolic effects, including MC-903, that the attenuated calcium effect may be due merely to more rapid metabolism of the vitamin reducing the amount of the circulating drug (see e.g. Bouillon et al., *J. Bone Miner. Res.* (1991), 6, p 1051 and Dusso et al., *Endocrinology* (1991), 128, p 1687). This may similarly reduce the cell modulating effect in vivo so that one may require larger systemic dosages than are suggested by in vitro test results.

Use of such analogues may therefore give rise to cumulative toxicity problems if the compounds are used in long term therapy, particularly where systemic application is required, e.g. for treatment of inflammatory and autoimmune diseases, neoplasias and hyperplasias, or in oral therapy for treatment of psoriasis, and there is thus a continuing need for vitamin D-like compounds which exhibit potent cell modulating activity coupled with a reduced effect on calcium metabolism.

The present invention is based on the surprising discovery of a number of 1α-hydroxy vitamin D derivatives in which the 17-position side chain carries an azide or a 1,2,3-triazole group (hereinafter for brevity referred to simply as a triazole group), which derivatives, while exhibiting minimal effect on calcium metabolism, may have a potent cell modulating effect, for example as evidenced by eliciting cell differentiation and maturation, inhibiting proliferation and/or by activating monocytes (e.g. as estimated by the method of Styrt et al., *Blood* (1986), 67, pp 334–342). Thus compounds according to the invention have been found to have insignificant effects on serum calcium and phosphorus levels in rats, even when administered in amounts of 100 times a conventional dosage for 1α,25-dihydroxy vitamin $D_3$, and accordingly exhibit an advantageous therapeutic ratio of cell modulating to calcaemic activity.

A further advantage of the compounds of the invention is that they have a very low affinity for the intestinal 1α,25-dihydroxycholecalciferol receptor.

The invention includes compounds of formula (I)

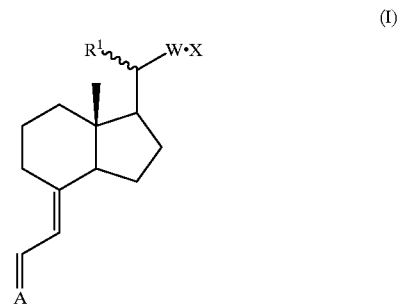

(where $R^1$ represents a methyl group having α- or β-configuration; W represents a valence bond or a $C_{1-5}$ alkylene group, e.g. a straight chained group such as methylene, ethylene, trimethylene, tetramethylene or pentamethylene; X represents azide or an optionally substituted triazole group; and A= represents a cyclohexylidene moiety characteristic of the A-ring of a 1α-hydroxylated vitamin D or analogue thereof.

The fact that compounds (I), which possess 17-position side chains of varying size not carrying any hydroxyl groups, exhibit cell modulating activity is unexpected in the light of previous findings in this area, which strongly suggest the necessity of such hydroxyl groups.

Furthermore, as noted by Kubodera et al. (op. cit., 1991), introduction of a nitrogen atom into the 17-position side chain of 1α,25-dihydroxy vitamin $D_3$ appears to be deactivating as regards differentiation-inducing activity. It might also be expected that the presence of a heterocyclic aryl group such as a triazole group would similarly be deactivating in view of the findings of Figadère et al., *J. Med. Chem.* (1991), 34, pp 2452–2463 that the presence of side chain carbocyclic aryl groups most commonly leads to reduced differentiation-inducing activity.

Where X in formula (I) represents a triazole group it will normally be linked to W through the 1-position nitrogen atom, and may be substituted, e.g. at the 4- or 5-position, for example by a carbamoyl or a primary, secondary or tertiary carbinol group, which substituent may optionally be linked to the triazole ring by a lower (e.g. $C_{1-3}$) alkylene group.

One such class of compounds according to the invention may be represented by the formula (II)

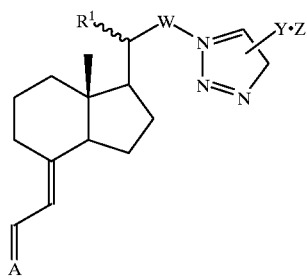

(II)

(wherein $R^1$, W and A= are as hereinbefore defined; Y represents a valence bond or a lower alkylene group attached to the 4- or 5-position of the triazole ring; and Z is (i) a group —$CO.NR^2R^3$ in which $R^2$ and $R^3$ may be the same or different and each represents a hydrogen atom or an aliphatic, cycloaliphatic, aralidhatic or aryl group or $R^2$ and $R^3$ together with the nitrogen atom to which they are attached form a heterocyclic group or (ii) a group —$C(R^4)(R^5).OH$ in which $R^4$ and $R^5$ may be the same or different and each represents a hydrogen atom or an aliphatic, cycloaliphatic, araliphatic or aryl group or $R^4$ and $R^5$ together with the carbon atom to which they are attached form a $C_{3-8}$ carbocyclic ring)

Where any of $R^2$–$R^5$ represent aliphatic groups these may, for example, be lower (e.g. $C_{1-6}$) alkyl groups such as methyl, ethyl, propyl and butyl groups. Cycloaliphatic groups may, for example, include lower cycloalkyl groups, for example containing 3–8 carbon atoms, e.g. as in cyclopropyl, cyclopentyl and cyclohexyl groups. Araliphatic groups may, for example, include $C_{6-12}$ aryl $C_{1-4}$ alkyl groups such as benzyl or phenethyl. Aryl groups may, for example, include $C_{6-12}$ carbocyclic aryl groups such as phenyl or naphthyl, optionally carrying one or more substituents, for example selected from halo (e.g. chloro or bromo), lower (e.g. $C_{1-4}$) alkyl such as methyl, lower alkoxy (e.g. methoxy), lower alkanoyl (e.g. acetyl), lower alkylamino (e.g. methylamino), di(lower alkyl)amino (e.g. dimethylamino), nitro, carbamoyl and lower alkanoylamino (e.g. acetamido).

Where the group $R^2R^3N$— represents a heterocyclic group this may, for example, contain one or more further heteroatoms selected from O, N and S and may comprise one or more rings, e.g. each having 5 or 6 ring members, for example as in N-attached pyrrolyl, pyrazolyl, imidazolyl, indolyl, indazolyl, purinyl, pyrrolidinyl, imidazolidinyl, pyrazolidinyl, piperidinyl, morpholino, thiazolidinyl or thiamorpholino groups.

Where the group —$C(R^4)(R^5)$— represents a carbocyclic ring this may for example be saturated as in cyclopropylidene, cyclopentylidene or cyclohexylidene or unsaturated as in cyclopentenylidene, cyclopentadienylidene or cyclohexenylidene.

The total number of carbon atoms present in W and Y preferably does not exceed 4.

Where $R^1$ in formulae (I) and (II) is a methyl group in the α- configuration the compounds have the 20R configuration characteristic of natural vitamin D derivatives; where $R^1$ is in the β-configuration the compounds have the 20S configuration of epi-vitamin D derivatives. It will be appreciated that the invention also embraces mixtures of the two isomers.

The cyclohexylidene ring represented by A= will normally carry hydroxyl groups or protected derivatives thereof at the 1α- and 3β-positions, and may carry further substituents, e.g. which tend to enhance antiproliferative activity and/or stimulate differentiation. A= may thus, for example, be represented by the formula (A-1)

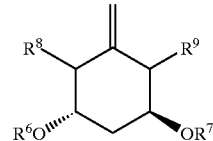

(A-1)

where $R^6$ and $R^7$, which may be the same or different, each represent a hydrogen atom or an O-protecting group, and $R^8$ and $R^9$, which may the same or different, are selected from hydrogen atoms and appropriate mono- or di-valent substituting groups.

Where $R^6$ and $R^7$ represent O-protecting groups these may, for example, be cleavable O-protecting groups such as are commonly known in the art. Suitable groups include etherifying groups such as silyl groups (e.g. tri (lower alkyl) silyl groups such as trimethylsilyl, triethylsilyl, triisopropylsilyl or t-butyldimethylsilyl; tri (aryl) silyl groups such as triphenylsilyl; and mixed alkyl-arylsilyl groups); lower (e.g. $C_{1-6}$) alkyl groups optionally interrupted by an oxygen atom, such as methyl, methoxymethyl or methoxyethoxymethyl; and cyclic groups such as tetrahydropyranyl. Esterifying O-protecting groups include lower (e.g. $C_{1-6}$) alkanoyl such as acetyl, propionyl, isobutyryl or pivaloyl; aroyl (e.g. containing 7–15 carbon atoms) such as benzoyl or 4-phenylazobenzoyl; lower alkane sulphonyl such as (optionally halogenated) methane sulphonyl; and arene sulphonyl such as p-toluene sulphonyl.

O-protected derivatives are useful as intermediates in the preparation of active 1α,3β-diols of formula (I) where $R^6$ and $R^7$ represent hydrogen atoms. Additionally, where the O-protecting groups are metabolically labile in vivo, such ethers and esters of formula (I) may be useful directly in therapy.

At least one of $R^8$ and $R^9$ is advantageously a hydrogen atom. Substituents which may be present as the other of $R^8$ and $R^9$ include, for example, methylene, methyl and spiroliked cyclopropyl groups.

Representative A= groups falling within the above formula (A-1) include the following:

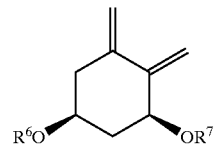

(A-2)

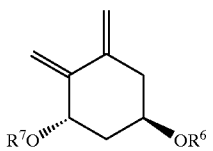

(A-3)

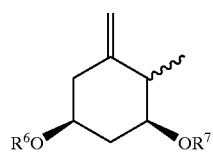
(A-4)

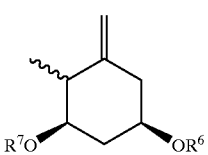
(A-5)

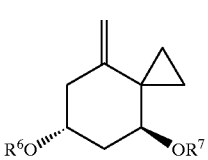
(A-6)

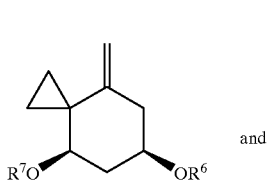
and
(A-7)

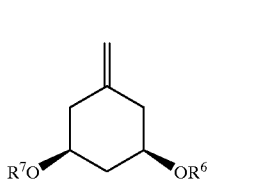
(A-8)

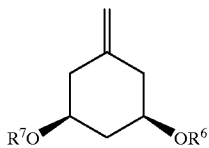

It will be appreciated that compounds containing groups (A-2) and (A-3) are respectively 5,6-cis (i.e. 5Z) and 5,6-trans (i.e. 5E) isomers of vitamin D analogues. Compounds containing groups (A-4) and (A-5) are similarly 5,6-cis and 5,6-trans isomers respectively of 10,19-dihydro vitamin D analogues, and compounds containing group (A-8) are 19-nor vitamin D analogues.

5,6-trans isomers according to the invention are particularly of interest as intermediates in the preparation of corresponding 5,6-cis isomers, e.g. as described in greater detail hereinafter. However, 5,6-trans isomers in which $R^6$ and $R^7$ are hydrogen atoms or metabolically labile groups will often exhibit cell modulating activity, e.g. at about one order of magnitude less than corresponding 5,6-cis isomers, and may thus be useful in therapy, especially as their effect in elevating serum calcium levels may also be reduced, thus maintaining an appreciable separation between cell modulating and calcaemic activities.

The cell modulating activity of active compounds according to the invention, combined with their substantial lack of calcaemic effect, render them of interest (both alone and as adjuncts) in the management of neoplastic disease, particularly myelogenous leukemias. They may also be used either alone or as adjuncts in the chemotherapy of infection and in all other therapeutic modalities in which mononuclear phagocytes are involved, for example in treatment of bone disease (e.g. osteoporosis, osteopenia and osteodystrophy as in rickets or renal osteodystrophy), autoimmune diseases, host-graft reaction, transplant rejection, inflammatory diseases (including modulation of immunoinflammatory reactions), neoplasias and hyperplasias, myopathy, enteropathy and spondylitic heart disease. Active compounds according to the invention may also be useful in promotion of wound healing, suppression of parathyroid hormone (e.g. as in serum calcium homeostasis), in treatment of dermatological diseases (for example including acne, alopecia, eczema, pruritus, psoriasis and skin aging (including photoaging), hypertension, rheumatoid arthritis, psoriatic arthritis, secondary hyperparathyroidism, asthma, cognitive impairment and senile dementia (including Alzheimer's disease), in fertility control in both human and animal subjects, and in management of disorders involving blood clotting, e.g. by dissolution of existing clots and/or prevention of clotting. The invention embraces use of these compounds in the therapy or prophylaxis of such conditions and in the manufacture of medicaments for such treatment or prophylaxis.

We believe that the active 20R isomers of formula (I) may be preferred for treatment of infections, e.g. in combination therapy, whereas the active 20S epi-isomers may be preferred for applications involving an immunosuppressive effect, e.g. in treatment of autoimmune and inflammatory diseases, rheumatoid arthritis, asthma etc. This view is supported by, for example, the work of Binderup et al. concerning 20-epi-vitamin $D_3$ analogues reported in *Biochemical Pharmacology* (1991), 42(8), pp 1569–1575.

It has been reported (Neef et al., 9th Workshop on Vitamin D (1994)) that in the case of vitamin D compounds having conventional terminally hydroxylated 17-position side chains (including side chains containing a heteroatom at the 23-position), analogues having 20,20-dimethyl, 20-methylene or 20-spirocyclopropyl groups may exhibit useful biological activity, typically resembling that of the corresponding 20R methyl-substituted isomer rather than the corresponding 20S epi-isomer. The present invention embraces analogues of the above-defined compounds of formulae (I) and (II) wherein $R_1$ is selected from dimethyl, methylene and spirocyclopropyl groups.

Active compounds according to the invention may be formulated for administration by any convenient route, e.g. orally (including sublingually), parenterally, rectally, topically or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for topical administration include ointments, creams, gels, lotions, shampoos, paints, powders (including spray powders), pessaries, tampons, sprays, dips, aerosols, pour-ons and drops. The active ingredient may, for example, be formulated in a hydrophilic or hydrophobic base as appropriate.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.5–2500 µg, e.g. 1–500 µg, of active compound according to the invention per unit dosage form. The compositions may if desired incorporate one or more further active ingredients.

A suitable daily dose of an active compound according to the invention may for example be in the range 1–5000 µg, e.g. 2–1000 µg, per day, depending on factors such as the severity of the condition being treated and the age, weight and condition of the subject.

Compounds according to the invention may be prepared by any convenient method, for example one of the following:

A) 5,6-Cis compounds of formula (I) may be prepared by isomerisation of a corresponding 5,6-trans compound, followed if necessary and/or desired by removal of any O-protecting groups. Isomerisation may be effected by, for example, treatment with iodine, with a disulphide or diselenide, or by irradiation with ultraviolet light, preferably in the presence of a triplet sensitiser.

B) 5,6-Trans compounds of formula (I) may be prepared by hydroxylating a corresponding 1-unsubstituted-5,6-trans compound, e.g. a compound (I) having an A= group of the formula

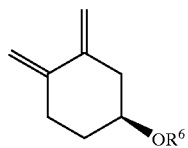

(A-9)

(where $R^6$ is hydrogen or an O-protecting group). Such hydroxylation may be effected using a selenite ester (which may be generated in situ by reaction of selenium is dioxide or selenous acid and an alcohol), e.g. as described in GB-A-2038834, or using selenous acid at a pH in the range 3–9, e.g. as described in GB-A-2108506; the contents of both these specifications are incorporated herein by reference. The 1-unsubstituted-5,6-trans compound may, if desired, be prepared by isomerisation of the corresponding 5,6-cis vitamin in situ under the conditions of the hydroxylation reaction, which may be followed by isomerisation and/or removal of O-protecting groups as necessary and/or desired.

C) By reaction of a compound containing a precursor for the desired 17-position side chain in one or more stages and with one or more reactants serving to form the desired side chain, followed if necessary and/or desired by isomerisation and/or removal of O-protecting groups.

Thus, for example, a compound of general formula (III)

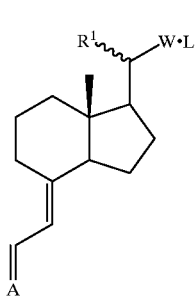

(III)

where $R^1$, W and A= are as hereinbefore defined, A= preferably being one of the groups (A-2)–(A-8) in O-protected form, and L represents a leaving group, for example a sulphonate ester group, e.g. lower alkyl sulphonyloxy such as mesyloxy, lower fluoroalkyl sulphonyloxy such as trifluoromethanesulphonyloxy or aryl sulphonyloxy such as tosyloxy, or a halogen atom such as chlorine, bromine or iodine) may be reacted with a source of azide ions, for example an alkali metal azide such as sodium or potassium azide, to yield a compound (I) in which X is an azide group. It should be noted that compounds (III) in which A= is as defined for (A-9) may also be employed and thereafter subjected to 1α-hydroxylation as described under (B) above.

The resulting azide of formula (I) may be subjected to a 1,3 dipolar cyclo-addition by reaction with an appropriately substituted acetylene derivative to yield a compound (I) in which X is a triazole group. Suitable acetylene derivatives include compounds of formula (IV)

CH≡C.Y.Z' (IV)

(where Y is as hereinbefore defined and Z' is as defined for Z or is an esterified carboxyl group, e.g. a lower alkoxycarbonyl group such as methoxycarbonyl or ethoxycarbonyl). Where Y in formula (IV) represents a valence bond, such cyclo-additions will tend to lead to compounds of formula (II) in which the substituent —Y.Z is predominantly at the 4-position, although a minor amount of the 5-substituted isomer may be isolatable. Where Y represents $CH_2$ or a higher homologue, 4- and 5-substituted isomers may be produced in approximately equal amounts. Such isomers may be separated by, for example, conventional methods such as chromatography.

Where a compound (IV) in which Z' is an esterified carboxyl group is employed, this group in the resulting triazole compound of formula (I) may be converted directly or indirectly to a group —$CO.NR^2R^3$ (where $R^2$ and $R^3$ are as hereinbefore defined). Indirect conversion may, for example, be effected by hydrolysing the ester to the corresponding acid and reacting this with an amine $R^2R^3NH$, e.g. in the presence of a coupling agent such as dicyclohexylcarbodiimide; alternatively the acid may be converted to a reactive derivative such as an acyl halide and thereafter reacted with the amine $R^2R^3NH$. Direct amide formation may be effected by reaction of the ester with the amine $R^2R^3NH$ but is more preferably performed using an activated metalated derivative thereof, e.g. a tin(II) amide as described by Wang et al. (*J. Org. Chem.* (1992), 57, pp 6101–6103).

Alternatively the ester group may be converted to a group —$C(R^4)(R^5).OH$ (where $R^4$ and $R^5$ are as hereinbefore defined). Where $R^4$ and $R^5$ both represent hydrogen atoms the conversion may be effected by reduction of the ester group, e.g. using a reducing agent such as lithium aluminium hydride or sodium in ethanol. Where $R^4$ and $R^5$ are identical groups the conversion may, for example, be effected by reaction with two moles of an appropriate organometallic compound, e.g. an organo lithium compound of formula $R^4Li$ or a corresponding Grignard reagent. Where $R^4$ and $R^5$ are different, the ester group may be hydrolysed to the corresponding acid, which is then converted to an acyl halide and reacted with a compound $R^4MX$ (where M represents a divalent metal such as copper, zinc or cadmium and X represents e.g. halogen) to generate the group —$CO.R^4$; reaction with a Grignard reagent $R^5MgX$ leads to formation of a desired —$C(R^4)(R^5).OH$ grouping; reduction, e.g. with a reducing agent such as sodium borohydride, leads to formation of a grouping in which $R^6$ represents a hydrogen atom.

Useful starting materials for the above compounds of formula (III) include compounds (V)

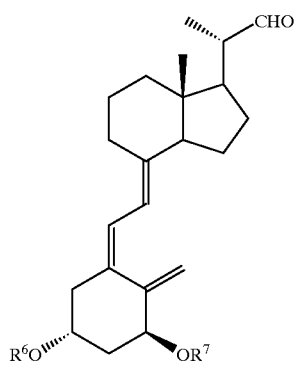

(V)

(where $R^6$ and $R^7$ are as defined above) and/or 5,6-trans isomers thereof and the corresponding 1-deoxy compounds;

such compounds may be obtained through oxidative cleavage (e.g. by ozonolysis) of the 22,23-double bond of vitamin $D_2$, 1α-hydroxy vitamin $D_2$ or O-protected derivatives thereof, these preferably being stabilised by formation of a Diels Alder dienophile adduct, e.g. with sulphur dioxide or a diazacyclo compound, for example as described in GB-A-2114570 (the contents of which are incorporated herein by reference).

Such 20S compounds (V), preferably still in the form of their dienodhile adducts, may be isomerised by, for example, treatment with a mild base, e.g. an inorganic base such as sodium bicarbonate or a tertiary organic base such as 1.4-diazabicyclo [2.2.2]octane ("DABCO") or 1,8-diazabicyclo [5.4.0]undec-7-ene ("DBU"). This yields a mixture of 20R and 20S isomers from which the pure 20R epi-isomer may be isolated chromatographically; alternatively separation of a desired epi-isomer may se delayed until a later stage in the synthesis, up to and including the final step.

Reduction of the aldehyde grouping of a compound (V) or a corresponding epi-isomer, e.g. using a metal hydride reducing agent such as sodium borohydride, yields a corresponding hydroxymethyl compound, i.e. a compound (III) in which W is $CH_2$ and L is OH. This may be converted to a compound (III) in which L is a leaving group by, for example, conversion to a sulphonate ester (e.g. to a tosylate) followed, if desired, by nucleophilic displacement of the sulphonate group by reaction with a halide salt (e.g. an alkali metal bromide).

Compounds (V) may also be oxidatively decarbonylated, e.g. as described in WO90/09991 using oxygen with cupric acetate, 2,2'-bipyridyl and DABCO as catalyst, to yield the corresponding 20-keto compound. This may be reduced to yield a 20-hydroxy compound which may in turn be converted to a compound (III) where W is a valence bond and L is a leaving group, e.g. by tosylation. The nature of the reducing agent with which the 20-ketone is reacted may influence the stereochemistry of the product; thus, for example, sodium borohydride tends to lead to a 20-hydroxy compound in which the 21-methyl group is in the β-configuration, whereas lithium aluminium hydride or sodium in ethanol favour formation of products where the 21-methyl group is in the α-configuration.

It will be appreciated that any subsequent reactions involving nucleophilic displacement of the 20-hydroxy group or a leaving group derived thereform will promote inversion of the configuration about the $C_{20}$ carbon atom. It will therefore be necessary to start from a configuration opposite to that ultimately desired where the reaction sequence involves an odd number of such nucleophilic displacements at $C_{20}$.

Compounds of formula (III) in which A= represents a group (A-9) as hereinbefore defined, W represents $CH_2$ or a valence bond, and L represents an O-protected hydroxyl group (e.g. in which the hydroxyl group is esterified, for example with a lower alkanoyl group such as acetyl) may be subjected to 1α-hydroxylation as described under (B) above to give compounds (III) in which A= represents a group (A-2) or (A-3) as hereinbefore defined in which $R^7$ represents hydrogen. Such compounds or protected derivatives thereof, e.g. in which $R^7$ is trimethylsilyl may be hydrogenated (e.g. in the presence of a noble metal catalyst such as tris-triphenylphosphine rhodium chloride) to yield corresponding compounds in which A= represents a group (A-4) or (A-5) as hereinbefore defined, or may be cyclopropanated (e.g. by reaction with methylene iodide in the presence of zinc/copper couple) to yield corresponding compounds in which A= represents a group (A-6) or (A-7) as hereinbefore defined. Where appropriate, the compounds so obtained may be converted to compounds in which $R^7$ is an O-protecting group (e.g. by silylation) and may be hydrolysed (e.g. with base such as potassium hydroxide or potassium carbonate) or reduced (e.g. with lithium aluminium hydride) to remove the side chain ester group to yield useful starting materials (III) in which L represents a hydroxyl group.

19-Nor analogues of compounds of formula (V) and corresponding 20-hydroxymethyl compounds (i.e. starting materials for compounds (I) in which A= represents a group (A-8) as hereinbefore defined) may be prepared as described by Perlman et al., *Tetrahedron Letters* (1992), 33, pp 2937–2940.

Higher homologues of formula (III), e.g. in which W is ethylene or trimethylene, may, for example, be obtained by reaction of a compound (III) in which W is methylene either (i) with a reagent serving to introduce a one-carbon fragment (e.g. a metal cyanide) and conversion of the group so introduced to a group —$CH_2L$, e.g. by hydrolysing a cyano group to yield a carboxy group or by reducing such a cyano group (e.g. with a metal hydride reducing agent such as diisobutyl aluminium hydride) to yield a carboxaldehyde group, and reducing the carboxy or carboxaldehyde group (e.g. using yield a hydroxymethyl group which may in turn be subjected to tosylation and, if desired, nucleophilic displacement as hereinbefore described to effect conversion to a halomethyl group; or (ii) with a metallated derivative of an ester or thioester of acetic acid, with a derivative containing another carbanionic equivalent of acetic acid (e.g. a metallated derivative of acetonitrile), or with a metallated malonate ester (in which last instance the reaction product is partially hydrolysed to yield a monoester which may be decarboxylated by heating to yield a carboxylate ester), reducing the resulting ester or thioester product to an alcohol (e.g. using lithium aluminium hydride), and converting the resulting hydroxyl group to a leaving group, such as a tosylate group or a halogen atom, e.g. as hereinbefore described.

It will be appreciated that the above procedures (i) and/or (ii) may be repeated to yield compounds (III) in which W is a $C_4$ or $C_5$ alkylene group.

Similar homologation techniques may be used to generate a desired Y grouping in compounds of formula (II). Thus, for example, a compound (II) in which Y represents a valence bond and Z is an esterified carboxyl group as hereinbefore defined for Z' may be reduced to the corresponding hydroxymethyl compound, e.g. using a metal hydride reducing agent such as lithium aluminium hydride. This compound may be converted to, for example, a tosyloxymethyl and thereafter a halomethyl derivative and reacted with a reagent such as a metal cyanide; hydrolysis of the cyano group so introduced to a carboxyl group may be followed by amide formation or esterification/Grignard/reduction reactions, e.g. as hereinbefore described, to yield compounds (II) in which Y represents a methylene group and Z is a group —$CO.NR^2R^3$ or —$C(R^4)(R^5).OH$ as hereinbefore defined; alternatively the carboxyl group may be esterified and the resulting compound (II) in which Y represents a methylene group and Z is an esterified carboxyl group may be subjected to one or more further homologation sequences.

Analogues of compounds (III) in which $R^1$ is selected from dimethyl, methylene and spirocyclopropyl groups (e.g. prepared in similar manner to that described by Neef et al., op. cit.) may be reacted as described above to prepare similar analogues of compounds of formulae (I) and/or (II). Minor modifications of reaction conditions may be made as necessary and/or desired; thus, for example, in analogues of compounds (III) in is which $R^1$ represents dimethyl and W represents $CH_2$, the group L is attached to a neopentyl-like carbon atom and a strong leaving group such as trifluoromethane sulphonate is preferred, whilst use of hydrogen bond donating solvents such as water, alcohols or amines should be avoided in order to minimise rearrangement at the 20-position carbon atom. Such modifications may not be necessary when reacting analogues of compounds (III) in which W represents $(CH_2)_2$ or a higher homologue.

D) By reaction of a compound of formula (I) to modify the substitution pattern about the A= group, followed if necessary and/or desired by isomerisation and/or removal of protecting groups.

Thus for example, compounds (I) in which A= represents a group (A-4) or (A-5) may be prepared by hydrogenation of corresponding compounds in which A= represents (A-2) or (A-3), e.g. using the method of GB-A-1583749. It will be appreciated that such hydrogenation may alternatively be effected at an earlier stage of a reaction sequence, e.g. on a starting material or intermediate of formula (III).

Compounds (I) in which A= represents a group (A-6) or (A-7) may be prepared from corresponding compounds in which A= represents (A-2) or (A-3) (in which $R^6$ is an O-protecting group and $R^5$ is a hydrogen atom or a trimethylsilyl group) by Simmons-Smith methylenation (see e.g. Neef et al., *Tetrahedron Letters* (1991), 32, pp 5073–5076).

Compounds (I) in which A= represents a group (A-8) may, for example, be prepared by cleavage of the 7,8-double bond of an appropriate vitamin D derivative (e.g. a precursor compound (I) in which A= is a group (A-9)), for example by ozonolysis or by successive reaction with potassium permanganate and sodium periodate, followed by Wittig-Horner reaction of the resulting 8-one with an appropriate ring A precursor, e.g. of formula (VI)

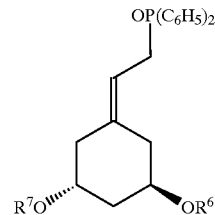

(VI)

(where $R^6$ and $R^7$ represent O-protecting groups)—see, for example, Perlman et al., *Tetrahedron Letters* (1992), 33, pp 2937–2940.

In general, either 5,6-cis or 5,6-trans geometry may be present at any of the various steps described in (C) and (D) above, although it may be preferred to employ 5,6-trans isomers in the above-mentioned 1α-hydroxylation and 22,23-double bond oxidative cleavage reactions. Conversion of 5,6-trans geometry to 5,6-cis is thus most advantageously effected after introduction of the 1α-hydroxyl group.

It will be appreciated that many of the reaction sequences described above may also be accomplished using appropriate steroid-5,5--dienes (or steroid-5-enes which are convertible into such dienes), followed by conversion of the steroid products into the desired vitamin D analogues, e.g. by irradiation with UV light.

In general, O-protecting groups present at the 1α- and/or 3β- positions may be removed by, for example, conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkyl ammonium fluoride. The use of such acid-labile but base-stable protecting groups may be of advantage when reacting compounds of formula (II), in view of the strongly basic conditions normally employed in the homologation steps used to build up the desired side chain.

The following non-limitative examples serve to illustrate the invention. All temperatures are in ° C.

Preparation 1 a) 20α-Acetoxymethyl-1α-hydroxy-3β-triisopropylsilyloxy-9,10-secopregna-5(E), 7-diene [Formula (III) —A= (A-5),$R^1$=α-$CH_3$,$R^6$=(i-Pr)$_3$ Si, $R^7$=H,L=O.CO.$CH_3$, W=$CH_2$]

A solution or tris-triphenylphosphine rhodium chloride (450 mg) in benzene (30 ml) (or in a 1:1 mixture of benzene add ethanol) is stirred under hydrogen until no further uptake is observed. A solution of 20α-acetoxymethyl-1α-hydroxy-3β-triisopropylsilyloxy-9,10-secopregna-5(E), 7,10(19)-triene [Formula (III)—A=(A-3), $R^1$=α-$CH_3$, $R^6$= (i-Pr)$_3$ Si, $R^7$=H, L=O.CO.$CH_3$, W=$CH_2$ — as an alternative the corresponding 1α-trimethylsilyl ether may be used] (500 mg; in benzene (30 ml) is added and the mixture stirred under hydrogen until 1 equivalent of hydrogen has been taken up (ca 21 ml). The title compounds are purified by chromatography [the 10(R) and 10(S) isomers may optionally be resolved at this stage] and have UV $\lambda_{max}$ ca. 243,251 and 261 nm, with ε=ca 35,000; 40,000 and 27,000 respectively.

1α,3β-Bis-triisopropylsilyloxy-20α-hydroxymethyl-9,10-secopregna-5(E), 7-diene[Formula (III) —A=(A-5), $R^1$=α-$CH_3$, $R^6$=$R^7$=(i-Pr)$_3$Si, L=OH, W=$CH_2$]

The diene from (a) above (ca 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride careful addition of saturated aqueous sodium sulphate) the reaction mixture is worked up to afford the title alcohol.

Preparation 2

1α,3β-Bis-triisopropylsilyloxy-20α-hydroxymethyl-9,10-secopregna-5(Z), 7-diene[Formula (III) —A= (A-4), $R^1$=α-$CH_3$, $R^6$=$R^7$=(i-Pr)$_3$Si, L=OH, W=$CH_2$]

The 5(E)-triene starting material in Preparation 1(a) is photoisomerised in benzene in the presence of phenazine by irradiation for 1 hour, to yield the corresponding 5(Z)-triene. This product is hydrogenated as described in Preparation 1(a) and silylated and deacetylated as described in Preparation 1(b) to give the title compound. UV $\lambda_{max}$ ca. 243, 251 and 261 nm with ε=ca. 35,000; 40,000 and 27,000 respectively.

The epi (i.e. 20β-hydroxymethyl) compounds corresponding to the products of Preparations 1 and 2 are prepared by the same procedures starting with the 20-epi compound 20β-acetoxymethyl-1α-hydroxy-3β-triisopropylsilyloxy-9,10-secopregna-5(E), 7,10(19)-triene [Formula (III—A=(A-3), $R^1$=β-$CH_3$, $R^6$=(i-Pr)$_3$ Si, $R^7$=H, L=O.CO.$CH_3$, W=$CH^2$]. This is itself prepared by isomerisaion of the 20-aldehyde obtained by ozonolysis of the sulpur dioxide adduct of vitamin D$_2$ followed by reduction and 1α-hydroxylation of the 20-epi aldehyde.

Preparation 3 a) 20α-Acetoxymethyl-1α-hydroxy-3β-triisopropylsilyloxy-10-spirocyclopropyl-9,10-secopregna-5(E), 7-diene [Formula (III) —A=(A-7), $R^1$=α-$CH_3$, $R^6$=(i-Pr)$_3$Si, $R^7$=H, L=O.CO.$CH_3$, W=$CH_2$]

A mixture of zinc/copper couple (1.08 g) and diiodomethane (0.9 ml) in ether (6 ml) is heated under reflux with stirring for 40 minutes. A solution of 20α-acetoxymethyl-1α-hydroxy-3β-triisopropylsilyloxy-9,10-secopregna-5(E), 7,10(19)-triene [Formula (III) —A=(A-3), $R^1$=α-$CH_3$, $R^6$=(i-Pr)$_3$ Si, $R^7$=H, L=O.CO.$CH_3$, W=$CH_2$—as an alternative the corresponding 1α-trimethylsilyl ether may be used] (ca 500 mg) in ether (9 ml) is added, and the mixture is stirred and heated under reflux until most of the starting material has disappeared (TLC control: usually about 4 hours for the 1α-trimethylsilyl ether, less for the 1α-hydroxy compound). The reaction mixture is filtered, the solvent removed and the product chromatographed to remove the remaining diiodomethane. The title compound has UV $\lambda_{max}$ ca. 246, 253 and 263 nm, with ε=ca. 29,000; 36,000 and 25,000 respectively.

b) 1α,3β-Bis-triisopropylsilyloxy-20α-hydroxymethyl-10-spirocyclopropyl-9,10-secopregna-5(E), 7-diene [Formula (III) —A=(A-7), $R^1$=α-$CH_3$, $R^6$=$R^7$=(i-Pr)$_3$ Si, L=OH, W $CH_2$]

The diene from (a) above (ca 500 mg) in dichloromethane (2 ml) is treated with chlorotriisopropylsilane (250 mg) and imidazole (350 mg) and the mixture stirred overnight at room temperature. After work up the crude bis-silyl ether is dissolved in tetrahydrofuran (10 ml), treated with lithium aluminium hydride (100 mg) and stirred at room temperature for 1–2 hours. After decomposition of the excess lithium aluminium hydride careful addition of saturated aqueous sodium sulphate) the reaction mixture is worked up to afford the title alcohol.

Preparation 4

1α,3β-Bis-triisoproplsilyloxy-20α-hydroxymethyl-10-spirocyclopropyl-9,10-secopregna-5(Z), 7-diene [Formula (III) —A=(A-6), $R^1$=α-$CH_3$, $R^6$=$R^7$=(i-Pr)$_3$ Si, L=OH, W=$CH_2$]

The procedure of Preparation 3(a) is repeated starting from the corresponding 5(Z)-triene, prepared by photoisomerization of the 5(E)-triene as described in Preparation 2; the reaction of the 5(Z)-triene is somewhat slower than that of the 5(E)-triene. Silylation and de-acetylation as described in Preparation 3(b) gives the title compound. UV $\lambda_{max}$ ca. 246, 253 and 263 nm with ε=ca. 29,000; 36,000 and 25,000 respectively.

Preparation 5

1α,3β-Bis-t-butyldimethylsilyloxy-20β-hydroxymethyl-19-nor-9,10-secopregna-5(E), 7-diene [Formula (III) —A=(A-8), $R^1$=β-$CH_3$, $R^6$=$R^7$=t-Bu(Me)$_2$Si, L=OH, W=$CH_2$]

1α,3β-Bis-t-butyldimethylsilyloxy-20α-formyl-19-nor-9,10-secopregna-5,7-diene [Formula (III) —A=(A-8), $R^1$=α-$CH_3$, $R^6$=$R^7$=t-Bu(Me)$_2$Si, L=CHO, W=valence bond] obtained as in *Tetrahedron Lett.* (1992), 33, p 2937, (about 1.5 g) is dissolved in benzene (15 ml) and methanol (15 ml) and isomerised by storage overnight with DBU (400 μl) at 0°. The mixture of normal (20α-formyl) and epi (20β-formyl) aldehydes may be resolved by chromatography silica eluted with 15% benzene in hexane) before or after reduction of the aldehyde (ca 1 g) in benzene (30 ml) by dropwise treatment with sodium borohydride, (400 mg) in ethanol (15 ml) at 0°, whereafter the reaction mixture is stirred at 0° for a further 0.5 hour. After work up the product is resolved by chromatography (silica gel eluting with benzene or ether in hexane) to yield the title compound.

Preparation 6 a) 1α,3β-Bis-triisopropylsilyloxy-23-nor-9,10-secochola-5(E), 7,10(19)-trienic acid, nitrile (mixture of 20- normal and 20- epi isomers) [Formula (III) —A=(A-3), $R^1$=α- and β-$CH_3$, $R^6$=$R^7$=(i-Pr)$_3$Si, L=CN, W=$CH_2$]

A solution of 1α,3β-bis-triisopropylsilyloxy-20(α,β)-tosyloxymethyl-9,10-secopregna-5(E), 7,10(19)-triene [Formula (III) —A=(A-3), $R^1$=α,β-$CH_3$, $R^6$=$R^7$=(i-Pr)$_3$Si, L=O.tosyl, W=$CH_2$] (1 g) in dimethylsulphoxide (5 ml) containing potassium cyanide (390 mg) was heated at 90° for 2 hours, and the product was extracted (diethyl ether), washed and purified by column chromatography to give the title nitrile (748 mg). UV (Et$_2$O) $\lambda_{max}$ 267, $\lambda_{min}$ 229 nm; NMR (CCl$_4$) δ5.36–6.13 (ABq, 6,7-H's), 4.83 (bs, 19-H's), 4.13–4.46 (m, 1,3-H's), 0.53 (s, 18-H's).

b) 1α,3β-Bis-triisopropylsilyloxy-23-nor-9,10-secochola-5(E), 7,10(19)-trienic carboxaldehyde, (mixture of 20- normal and 20- epi isomers) [Formula (III) —A=(A-3), $R^1$=α- and β-$CH_3$, $R^6$=$R^7$=(i-Pr)$_3$Si—, L=CHO, W =$CH_2$]

The nitrile from (a) above (480 mg) in hexane (3 ml) was cooled to –78° and treated with diisobutylaluminium hydride (1.4 ml of a 1M solution in heptane). The mixture was stirred at 0° for 1 hour, treated with ether and saturated ammonium chloride solution, and the product isolated by extraction into ether. The crude product had UV (Et$_2$O) $\lambda_{max}$ 270, $\lambda_{min}$ 229 nm; IR (CCl$_4$) $\nu_{max}$ 1730 cm$^{-1}$; NMR (CCl$_4$) δ10.6 (bs, CHO), 5.53–6.23 (ABq, 6,7-H's), 4.76 (bs, 19-H's), 4.16–4.43 (m, 1,3-H's), 0.56 (s, 18-H's).

c) 1α,3β-Bis-triisotropylsilyloxy-20(α,β)-(2-hydroxyethyl)-9,10-secopregna-5(E), 7,10(19)-triene [Formula (III) —A=(A-3), $R^1$=α- and β-$CH_3$, $R^6$=$R^7$=(i-Pr)$_3$Si, L=OH, W=$(CH_2)_2$]

The aldehyde from (b) above (440 mg) in benzene (10 ml) was treated at 0° with a solution of sodium borohydride (105 mg) in ethanol (10 ml) followed by stirring at room temperature for 45 minutes. After work up the product was purified by chromatography to give the title compound (380 mg). UV (Et$_2$O) $\lambda_{max}$ 269, $\lambda_{min}$ 228 nm; IR (CCl$_4$) $\nu_{max}$ 3500–3700 cm$^{-1}$; NMR (CCl$_4$) δ5.5.53–6.3 (ABq, 6,7-H's), 4.73 (bs, 19-H's), 4.16–4.43 (m, 1,3-H's), 0.56 (s, 18-H's).

The isomers (at C-20) were resolved by careful chromatography of 1.2 g of mixture on silica gel developed with 30% benzene in hexane. The 20β-(epi) isomer (145 mg) was less polar and eluted first followed by a mixture of isomers and then the 20α-(normal) isomer (360 mg).

Preparation 7 a) 4-Ethylhex-2-yn-4-ol

A solution of methyl 2-butynoate (1.5 g) in ether (50 ml) was cooled to 0°, treated with ethyl magnesium bromide (21 ml of a 3M solution in ether) and stirred at room temperature for 4 hours. The mixture was then cooled to 0° and treated with saturated ammonium chloride solution, whereafter the product was extracted into ether and the title compound (1.2 g) was isolated by chromatography. IR (CCl$_4$) $\nu_{max}$ 2200 (C≡C), 3450 cm$^{-1}$ (OH); NMR (CCl$_4$) δ1.83 (s, H$_3$C—C≡), 2.3 (s), 1.36–1.6 (m, CH$_2$CH$_3$), 0.93 t, CH$_3$CH$_2$).

b) 4-Ethylhex-1-yn-4-ol [Formula (IV) —Y=$CH_2$, Z'=—C($R^4$)($R^5$).OH where $R^4$=$R^5$=$C_2H_5$]

This isomerisation, using the "Acetylene Zipper", was adapted from the procedure of Brown et al., *J. Chem. Soc. Chem. Comm.* 1976), p. 959. Potassium hydride (3.42 ml of a 35% suspension in mineral oil) was washed three times with hexane (3 ml portions) to remove the oil, cooled to 0° and treated with 1,3-diaminopropane (25 ml). The resulting mixture was stirred for 1 hour at room temperature and then cooled to 0°. The product from (a) above (600 mg was added and the mixture was stirred for 2 hours at 0° and then kept at room temperature for a further hour. The product was extracted into ether, washed many times with water to remove the diamine, concentrated in vacuo and isolated by chromatography to give the title compound (350 mg). IR (CCl$_4$) $\nu_{max}$ 2200 (C≡C), 3310 cm$^{-1}$ H—C≡); NMR (CCl$_4$) δ1.9 (vnt, H—C≡), 2.23 (t, ≡C—CH$_2$—) 1.4–1.73 (m, CH$_2$CH$_3$), 0.82 (t, CH$_3$CH$_2$)

The compound 5-methylhex-1-yn-5-ol [Formula (IV) —Y=$(CH_2)_2$, Z'=—C($R^4$)($R^5$).OH where $R^4$=$R^5$=$CH_3$] is obtained by reacting ethyl 2-hexynoate and ethyl magnesium bromide in accordance with (a) above and isomerising the product in accordance with (b) above.

The compound 6-ethyloct-1-yn-6-ol [Formula (IV) —Y=$(CH_2)_3$, Z'=—C($R^4$)($R^5$).OH where $R^4$=$R^5$=$C_2H_5$] is obtained by reacting ethyl 2-hexynoate and ethyl magnesium bromide in accordance with (a) above and isomerising the product in accordance with (b) above.

The compound 4-methylhept-1-yn-4-ol [Formula (IV)—Y=$CH_2$, Z'=—C($R^4$)($R^5$).OH where $R^4$=$CH_3$, $R^5$=n-$C_3H_7$] is obtained by isomerising 4-methylhept-2-yn-4-ol in accordance with (b) above.

EXAMPLE 1 a) 20α-(3-Azidopropyl)-1α,3β-bis-triisopropylsilyloxy-9,10-secopregna-5(E), 7,10(19)-triene [Formula (I) —A=(A-3), $R^1$=α-$CH_3$, $R^6$=$R^7$=(i-Pr)$_3$Si, W=$(CH_2)_3$, X=$N_3$]

A solution of 1α,3β-bis-triisopropylsilyloxy-20α-(3-hydroxypropyl)-9,10-secopregna-5(E), 7,10 (19)-triene [Formula (III) —A=(A-3), $R^1$=α-$CH_3$, $R^6$=$R^7$=(i-Pr)$_3$Si, L=OH, W=$(CH_2)_3$] (140 mg) in methylene chloride (2 ml) was treated with 1,8-bis-dimethylaminonaphthalene (128 mg), cooled to –78°, and then treated with trifluoromethane-sulfonic anhydride (50 μl). The reaction mixture was allowed to warm to room temperature over a period of 15 minutes, then treated (vigorous stirring) with a solution of sodium azide (130 mg) and tetrabutylammonium bromide (5 mg) in water (2 ml). After 30 minutes the reaction mixture was diluted with water, the product extracted into ether and purified by chromatography to afford the title compound (117 mg). IR (CCl$_4$) $\nu_{max}$2100 cm$^{-1}$; UV (Et$_2$O) $\lambda_{max}$269, $\lambda_{min}$230 nm; NMR (CCl$_4$) δ5.56–6.3 (2H, ABq, 6,7-H's), 4.8 (2H, bs, 19-H's), 4.06–4.46 (2H, m, 1,3-H's), 0.56 (3H, s, 18-H's).

b) 20β-(3-Azidopropyl)-1α,3β-bis-triisopropylsilyloxy-9,10-secopregna-5(Z),7,10(19)-triene [Formula (I) —A=(A-2), $R^1$=α-$CH_3$, $R^6$=$R^7$=(i-Pr)$_3$, X=$N_3$]

A solution of the compound from (a) above (117 mg) in benzene (16.5 ml) containing phenazine (30 mg) and triethylamine (2 drops) was irradiated for 30 minutes. The solvent was then removed in vacuo and the product isolated by preparative thin layer chromatography (PLC) to afford the title compound (76 mg). IR (CCl$_4$) $\nu_{max}$2100 cm$^{-1}$; UV (Et$_2$O) $\lambda_{max}$263, $\lambda_{min}$227 nm; NMR (CCl$_4$) δ5.73–6.33 (2H, ABq, 6,7-H's), 4.73, 5.06 (each 1H, s, 19-H's), 4.06–4.46 (2H, m, 1,3-H's), 0.5 (3H, s, 18-H's)

c) 20α-(3-Azidopropyl)-1α,3β-dihydroxy-9,10-secopregna-5(Z),7,10(19)-triene [Formula (I) —A=(A-2), $R^1$=α-$CH_3$, $R^6$=$R^7$=H, W=$(CH_2)_3$]

A solution of the silyl ether from (b) above (76 mg) in tetrahydrofuran (THF) (0.5 ml) was treated with a solution of tetrabutylammonium fluoride in THF (1 ml, 1.0 M) and then stirred at room temperature for 2 hours. The solvent was removed, the product dissolved in methylene chloride, washed with water, and purified by PLC to afford the title compound (36 mg). IR (CDCl$_3$) $\nu_{max}$ 2100 cm$^{-1}$; UV (EtOH) $\lambda_{max}$264, $\lambda_{min}$ 227 nm; NMR (CDCl$_3$) δ5.86–6.3 (2H, ABq, 6,7-H's), 4.91, 5.25 (each 1H's, 19-H's), 0.93, 0.86 (d, 21-H's), 0.53 (3H, s, 18-H's).

EXAMPLE 2

20α-Azidomethyl-1α,3β-bis-triisopropylsilyloxy-9,10-secopregna-5(E), 7,10(19)-triene [Formula (I) —A=(A-3) $R^1$=α-$CH_3$, $R^6$=$R^7$=(i-Pr)$_3$Si, W=$CH_2$, X=$N_3$]

A solution of 1α,3β-bis-triisopropylsilyloxy-20α-tosyloxymethyl-9,10-secopregna-5(E), 7,10(19)-triene [Formula (III) —A=(A-3), $R^1$=α-$CH_3$, $R^6$=$R^7$=(i-Pr)$_3$Si, L=OTs, W=$CH_2$] (200 mg) in benzene (2.5 ml) was treated with a solution of sodium azide, (650 mg) and tetrabutylammonium bromide (10 mg) in water (2.5 ml) and then heated with stirring at 80° for 48 hours. The reaction mixture was then cooled, diluted with water and the product extracted into ether. Column chromatography of the ethereal extract afforded the title compound (115 mg). IR (CCl$_4$) $\lambda_{max}$2100 cm$^{-1}$; (N$_3$); UV (Et$_2$O) $\lambda_{max}$269 nm (23600); NMR (CCl$_4$) δ6.23, 5.63 (2H, ABq, 6,7-H's), 4.83 (2H, s, 19-H's), 4.66–4.0 (2H, m, 1,3-H's), 0.53 (3H, s, 18-H's)

The compound 20α-azidomethyl-1α,3β-bis-triisopropylsilyloxy-9,10-secopregna-5(E), 7-diene [Formula (I) —A=(A-5), $R^1$=α-$CH_3$, $R^6$=$R^7$=(i-Pr)$_3$ Si, W=$CH_2$, X=$N_3$] is prepared by similar reaction of the tosylated product of Preparation 1(b).

The compound 20α-azidomethyl-1α,3β-bis-triisopropylsilyloxy-9,10-secopregna-5(Z), 7-diene [Formula (I) —A=(A-4), $R^1$=α-$CH_3$, $R^6$=$R^7$=(i-Pr)$_3$ Si, W=$CH_2$, X=$N_3$] is prepared by similar reaction of the tosylated product of Preparation 2.

The compound 20α-azidomethyl-1α,3β-bis-triisopropylsilyloxy-10-spirocyclopropyl-9,10-secopregna-5(E), 7-diene [Formula (I) —A=(A-7), $R^1$=α-$CH_3$, $R^6$=$R^7$=(i-Pr)$_3$ Si, W=$CH_2$, X=$N_3$] is prepared by similar reaction of the tosylated product of Preparation 3(b).

The compound 20α-azidomethyl-1α,3β-bis-triisopropylsilyloxy-10-spirocyclopropyl-9,10-secopregna-5(Z), 7-diene [Formula (I) —A=(A-6), $R^1$=α-$CH_3$, $R^6$=$R^7$=(i-Pr)$_3$ Si, W=$CH_2$, X=$N_3$] is prepared by similar reaction of the tosylated product of Preparation 4.

The compound 20β-azidomethyl-1α,3β-bis-t-butyldimethylsilyloxy-19-nor-9,10-secopregna-5,7-diene [Formula (I) —A=(A-8), $R^1$=α-$CH_3$. $R^6$=$R^7$=t-Bu(Me)$_2$ Si, W=$CH_2$, X=$N_3$] is prepared by similar reaction of the tosylated product of Preparation 5.

EXAMPLE 3

20(α,β)-Azidomethyl-1α,3β-bis-triisopropylsilyloxy-9,10-secopregna-5(E), 7,10(19)-triene [Formula (I) —A=(A-3), $R^1$=α- and β-$CH_3$, $R^6$=$R^7$=(i-Pr)$_3$Si, W =$CH_2$, X=$N_3$]

A mixture of 1α,3β-bis-triisopropylsilyloxy-20α- and 20β-tosyloxymethyl-9,10-secopregna-5(E), 7,10(19)-triene [Formula (III) —A=(A-3), $R^1$=α,β-$CH_3$, $R^6$=$R^7$=(i-Pr)$_3$Si, L=OTs, W=$CH_2$] (335 mg) in benzene (4 ml) containing tetrabutylammonium bromide (26 mg) and 1,8-bis-dimethylamino-naphthalene ("proton sponge"—20 mg) was heated under reflux for 16 hours in the presence of sodium azide (1.09 g) and water (4 ml), and the product was purified by chromatography. Two such reactions gave the title compound (520 mg). UV (Et$_2$O) $\lambda_{max}$269, $\lambda_{min}$227 nm; IR (CCl$_4$) $v_{max}$2100 cm$^{-1}$; NMR (CCl$_4$) δ5.53–6.3 (ABq, 6,7-H's), 4.8(bs, 19-H's), 4.06–4.46 (m, 1,3-H's), 0.56 (s, 18-H's).

EXAMPLE 4 a) 1α-Hydroxy-20-oxo-3β-triisopropylsilyloxy-9,10-secopregna-5(E), 7,10(19)-triene A solution of selenium dioxide (112 mg) in methanol (7 ml) was added dropwise to a refluxing solution of 20-oxo-3β-triisopropylsilyloxy-9,10-secopregna-5(E), 7,10 (19)-triene (525 mg), 4-methylmorpholine-N-oxide (576 mg) and morpholine (100 μl) in methylene chloride (7 ml) and ethylene chloride (7 ml). Heating was continued for 6 hours, then the solution was cooled, treated with saturated aqueous sodium bicarbonate, the product extracted into methylene chloride, dried and purified by column chromatography to afford the title compound (312 mg). NMR (CCl$_4$) δ6.5–5.5 (2H, ABq, 6,7-H's), 4.8 (2H, d, 19-H's), 4.6–3.8 (2H, m, 1,3-H's), 2.0 (3H, s, 21-H's), 0.47 (3H, s, 18-H's); IR (CCl$_4$) $v_{max}$3300–3700 (OH), 1710 (C=O), 1620 cm$^{-1}$ UV (Et$_2$O) $\lambda_{max}$270 nm.

b) 20-Oxo-1α,3β-bis-triisopropylsilyloxy-9,10-secopregna-5(E), 7,10(19)-triene

The product from (a) above (680 mg) was stirred with chlorotriisopropylsilane (376 mg) and imidazole (530 mg) in methylene chloride (4 ml) overnight. The reaction mixture was then worked up and the product isolated by chromatography to give the title compound (890 mg). NMR (CCl$_4$) δ6.5–5.5 (2H, ABq, 6,7-H's), 4.8 (2H, s, 18-H's), 4.7–4.0 (2H, m, 1,3-H's), 2.0 (3H, s, 21-H's), 0.47 (3H, s, 18-H's); IR (CCl$_4$) $v_{max}$1710 (C=O), 1620 cm$^{-1}$; UV (Et$_2$O) $\lambda_{max}$269 nm.

c) 20β-Hydroxy-1α,3β-bis-triisopropylsilyloxy-9,10-secopregna-5(E), 7,10(19)-triene [Formula (III) —A=(A-3). $R^1$=β-$CH_3$. $R^6$=$R^7$=(i-Pr)$_3$Si, W=valence bond. L=OH]

A solution of the 20-ketone from (b) above (890 mg) in methanol (100 ml) was treated with sodium borohydride (100 mg, added in portions), stirred at room temperature for 30 minutes, then treated with acetic acid (0.5 ml). The methanol was removed in vacuo, water was added, and the product was extracted into methylene chloride washed with water then brine, dried and concentrated in vacuo. Isolation by column chromatography afforded the title compound (760 mg). NMR (CCl$_4$) δ6.4–5.4 (2H, ABq, 6,7-H's), 4.8 (2H, s, 19-H's), 4.7–4.0 (2H, m, 1,3-H's), 3.8–3.2 (1H, bm, 20α-H); 0.6 (3H, s, 18-H's); IR (CCl$_4$) $v_{max}$3300–3700 (OH), 1620 cm$^{-1}$; UV (Et$_2$O) $\lambda_{max}$269 nm.

d) 20α-Azido-1α,3β-bis-triisopropylsilyloxy-9,10-secopregna-5(E), 7,10(19)-triene [Formula (I) —A=(A-3), $R^1$=α-$CH_3$, $R^6$=$R^7$=(i-Pr)$_3$Si, W=valence bond, X=$N_3$]

A solution of the 20β-alcohol from (c) above (288 mg) in methylene chloride (2 ml) was treated with p-toluenesulphonyl chloride (177 mg) and pyridine (1 ml) and stirred at room temperature overnight. Saturated aqueous sodium bicarbonate was then added and after a further 3 hours the product was extracted into methylene chloride, washed successively with water, 5% aqueous hydrochloric acid, water, and brine, dried and concentrated in vacuo. The crude tosylate was, without further purification, treated with sodium azide (195 mg) in hexamethylphosphoramide (6 ml) and stirred at 85° for 3.5 hours. Water was added, the product extracted into methylene chloride, washed with water and brine, dried, concentred in vacuo and purified by chromatography to afford the title compound (85 mg). NMR (CCl$_4$) δ6.5–5.57 (2H, ABq, 6,7-H's), 4.85 (2H, s, 19-H's), 4.7–4.0 (2H, m, 1,3-H's), 3.4–3.0 (1H, bm, 20α-H), 1.3 (3H, d, 21-H), 0.57 (3H, s, 18-H's); IR (CCl$_3$) $v_{max}$2100 (N$_3$), 1620 cm$^{-1}$; UV (Et$_2$O) $\lambda_{max}$268 nm. (30% of the corresponding 5,7,10(19), 17(20)-tetraene was recovered as a by product).

e) 20α-Azido-1α,3β-bis-triisopropylsilyloxy-9,10-secopregna-5(Z),7,10(19)-triene [Formula (I) —A=(A-2), $R^1$=-α-$CH_3$, $R^6$=$R^7$=(i-Pr)$_3$Si, W=valence bond, X=$N_3$]

The azide from (d) above (54 mg) in benzene (8 ml) containing phenazine (32 mg) and triethylamine (2 drops) was irradiated for 1 hour at room temperature. The solvent was removed in vacuo and the product purified by preparative TLC to afford the title compound (46 mg). NMR (CCl$_4$) δ6.4–5.6 (2H, ABq, 6,7-H's), 4.77 and 5.1 (each 1H, bs, 19-H's), 4.45–4.0 (2H, m, 1,3-H's), 1.37 (3H, d, 21-H), 0.57 (3H, s, 18-H's); IR (CCl$_3$) $v_{max}$2100 (N$_3$), 1630 cm$^{-1}$; UV (Et$_2$O) $\lambda_{max}$263 nm.

f) 20α-Azido-1α,3β-dihydroxy-9,10-secopregna-5(Z),7,10 (19)-triene [Formula (I) —A=(A-2), $R^1$=α-$CH_3$, $R^6$=$R^7$=H, W=valence bond, X=$N_3$]

The silyl ether from (e) above (46 mg) was desilylated by treatment with tetrabutylammonium fluoride (0.6 ml of a 1 N solution in THF) and THF (0.6 ml). The product was purified by preparative TLC to afford the title compound (23 mg). NMR (CDCl$_3$) δ6.4–5.7 (2H, ABq, 6,7-H's), 4.87 and 5.27 (each 1H, bs, 19-H's), 4.5–4.0 (2H, m, 1,3- H's), 3.4–3.0 (1H, bm, 20-H), 1.3 (3H, d, 21-H), 0.53 (3H, s, 18-H's); IR (CCl$_3$) $v_{max}$3100–3650 (OH), 2100 ($N_3$), 1640 cm$^{-1}$; UV (Et$_2$O) $\lambda_{max}$263 nm.

EXAMPLE 5 a) 20α-(4-Methoxycarbonyl-1,2,3-triazol-1-yl)-1α,3β-bis-triisopropylsilyloxy-9,10-secopregna-5(E), 7,10(19)-triene [Formula (II) —A=(A-3), $R^1$=α-$CH_3$, $R^6$=$R^7$=(i-Pr)$_3$Si, W=valence bond, Y=valence bond, Z=4-CO.OCH$_3$]

A mixture of the 20α-azide from Example 4(d) (67 mg), methyl propiolate [Formula (IV) —Y=valence bond, Z'=CO.OCH$_3$] (0.75 ml) and benzene (0.25 ml) was stirred at room temperature for 30 hours. The solvent and excess reagent were removed under reduced pressure and the crude product mixture resolved by TLC to afford unreacted azide (13 mg), the triazole derivative isomeric to the title compound (having a 5-methoxy-carbonyl group) (6 mg) and the title compound (48 mg). UV (Et$_2$O) $\lambda_{max}$269, $\lambda_{min}$236 nm; IR (CCl$_4$) $v_{max}$1740 cm$^{-1}$; NMR (CCl$_4$) δ7.6 (1H, s, triazole-H), 5.3–6.4 (2H, ABq, 6,7-H's), 4.6–4.9 (2H, bs, 19-H's), 3.9–4.6 (2H, bm, 1,3-H's), 3.77 (3H, s, O—$CH_3$), 0.67 (3H, s, 18-H's).

b) 20α[4-(2-Hydroxyprop-2-yl)-1,2,3-triazol-1-yl]-1α,3β-bis-triisoiropylsilyloxy-9,10-secopregna-5(E), 7,10(19)-triene [Formula (II) —A=(A-3), $R^1$=α-$CH_3$, $R^6$=$R^7$=(i-Pr)$_3$Si, W=valence bond, Y=valence bond, Z=4-C($CH_3$)$_2$OH]

Methyl magnesium bromide (0.5 ml of a 3M solution in THF) was added dropwise to a solution of the product from (a) above (86 mg) in THF (1 ml) at 0°. The mixture was then stirred at room temperature for 2 hours, cooled, worked up and the product isolated by chromatography to give the title compound (69 mg). UV (Et$_2$O) $\lambda_{max}$269, $\lambda_{min}$230 nm; IR (CCl$_4$) $v_{max}$3200–3640 cm$^{-1}$; NMR (CCl$_4$) δ7.07 (1H, s, triazole-H), 5.4–6.4 (2H, ABq, 6,7-H's), 4.6–4.9 (2H, bs, 19-H's), 3.9–4.6 (2H, bm, 1,3-H's), 1.5 (6H, s, gem di-Me), 0.67 (3H, s, 18-H's).

c) 20α-[4-(2-Hyroxyprop-2-yl)-1,2,3-triazol-1-yl]-1α,3β-bis-triisopropylsilyloxy-9,10-secopregna-5(Z),7,10(19)-triene [Formula (II) —A=(A-2), $R^1$=α-$CH_3$; $R^6$=$R^7$=(i-Pr)$_3$Si, W=valence bond, Y=valence bond, Z=4-C($CH_3$)$_2$OH]

A mixture of the product from (b) above (69 mg) and phenazine (36 mg) in benzene (9 ml) was irradiated at room temperature for 120 minutes. Removal of the solvent and chromatography gave the title compound (53 mg). UV (Et$_2$O) $\lambda_{max}$262, $\lambda_{min}$229 nm; IR (CCl$_4$) $v_{max}$3200–3620 cm$^{-1}$; NMR (CCl$_4$) δ7.07 (1H, s, triazole-H), 5.6–6.3 (2H, ABq, 6,7-H's), 4.5–5.2 (each 1H, s, 19-H's), 3.9–4.5 (2H, bm, 1,3-H's), 1.5 (6H, s, gem di-Me), 0.63 (3H, s, 18-H's).

d) 1α,3β-Dihydroxy-20α-[4-(2-hydroxyprop-2-yl)-1,2,3-triazol-1-yl]-9,10-secopregna-5(Z),7,10(19)-triene [Formula (II) —A=(A-2), $R^1$=α-$CH_3$, $R^6$=$R^7$=H, W=valence bond, Y=valence bond, Z=4-C($CH_3$-$_2$OH The product from (c) above (54 mg) in THF was treated at room temperature with tetrabutylammonium fluoride (0.6 ml of a 1M solution in THF). The product was worked up and isolated by TLC (5t methanol in ethyl acetate) to give the title compound (30 mg). UV (EtOH) $\lambda_{max}$262, $\lambda_{min}$229 nm; IR (CDCl$_3$) vmax3200–3620 cm$^{-1}$; NMR (CDCl$_3$) δ7.23 (1H, s, triazole-H), 5.6–6.4 (2H, ABq, 6,7-H's), 4.8–5.3 (each 1H, s, 19-H's), 3.7–4.7 (2H, bm, 1,3-H's), 1.6 (6H, s, gem di-Me), 0.98 (d, 21-H's), 0.63 (3H, s, 18-H's)

EXAMPLE 6 a) 20α-[4-(3-Hydroxypent-3-yl)-1,2,3-triazol-1-yl]-1α,3β-bis-triisopropylsilyloxy-9,10-secopregna-5(E), 7,10(19)-triene [Formula (II) —A=(A-3), $R^1$=α-$CH_3$, $R^6$=$R^7$=(i-Pr)$_3$Si, W=valence bond, Y=valence bond, Z=4-C($C_2H_5$)$_2$OH]

Ethyl magnesium bromide (1.5 ml of a 1 M solution in THF) was added dropwise to a solution of the product from Example 5(a) (107 mg) in THF at 0°. The mixture was then stirred at room temperature for 2 hours, cooled, worked up and the product isolated by chromatography to give the title compound (64 mg). UV (Et$_2$O) $\lambda_{max}$267, $\lambda_{min}$238 nm; IR (CCl$_4$) $v_{max}$3200–3600 cm$^{-1}$; NMR (CCl$_4$) δ7.07 (1H, s, triazole-H), 5.4–6.4 (2H, ABq, 6,7-H's), 4 6–4.9 (2H, bs, 19-H's), 3.8–4.6 (2H, bm, 1,3-H's).

b) 20α-[4-(3-Hydroxypent-3-yl)-1,2,3-triazol-1-yl]-1α,3β-bis-triisopropylsilyloxy-9,10-secopregna-5(Z),7,10(19)-triene [Formula (II) —A=(A-2), $R^1$=α-$CH_3$, $R^6$=$R^7$=(i-Pr)$_3$Si, W=valence bond, Y=valence bond, Z=4-C($C_2H_5$)$_2$OH]

The 5(E)-isomer from (a) above (64 mg) in benzene (9 ml) was irradiated in the presence of phenazine (29 mg) and worked up as in Example 5(c) to afford the title compound (45 mg). UV (Et$_2$O) $\lambda_{max}$263, $\lambda_{min}$228 nm; IR (CCl$_4$) $v_{max}$3300–3640 cm$^{-1}$; NMR (CCl$_4$) δ6.97 (1H, s, triazole-H), 5.5–6.2 (2H, ABq, 6,7-H's), 4.5–5.1 (2H, bs, 19-H's), 3.9–4.5 (2H, bm, 1,3-H's).

c) 1α,3β-Dihydroxy-20α-[4-(3-hydroxypent-3-yl)-1,2,3-triazol-1-yl]-9,10-secopregna-5(Z),7,10(19)-triene [Formula (II) —A=(A-2), $R^1$=α-$CH_3$, $R^6$=$R^7$=H, W=valence bond, Y=valence bond, Z=4-C($C_2H_5$)$_2$OH]

The silyl ether from (b) above (45 mg) was desilyated with tetrabutylammonium fluoride in THF and worked up as in Example 5(d). TLC (methanol/ethyl acetate—1:20) gave the title compound (25 mg). UV (EtOH) $\lambda_{max}$262, $\lambda_{min}$229 nm; IR (CDCl$_3$) $v_{max}$3200–3660 cm$^{-1}$; NMR (CDCl$_3$) δ7.1 (1H, s, triazole-H), 5.7–6.6 (2H, ABq, 6,7-H's), 4.8–5.3 (each 1H, s, 19-H's), 3.8–4.8 (2H, bm, 1,3-H's), 0.8 (t, gem di-Et), 0.67 (3H, s, 18-H's).

EXAMPLE 7 a) 20α-(4-Methoxycarbonyl-1,2,3-triazol-1-ylmethyl)-1α,3β-bis-triisopropylsilyloxy-9,10-secopregna-5(E), 7,10(19)-triene [Formula (II) —A=(A-3), $R^1$α=-$CH_3$, $R^6$=$R^7$=(i-Pr)$_3$Si, W=$CH_2$, Y=valence bond, Z=4-CO.OCH$_{31}$]

A mixture of the 20α-azide from Example 2 (115 mg), methyl propiolate [Formula (IV) —Y=valence bond, Z'=CO.OCH$_3$] (1 ml) and benzene (0.25 ml) was stirred at room temperature for 2 days and worked up as in Example 5(a) to give the title compound (75 mg). UV (Et$_2$O) $\lambda_{max}$268, $\lambda_{min}$236 nm; IR (CCl$_4$) $v_{max}$1730 cm$^{-1}$; NMR (CCl$_4$) δ7.76 (1H, s, triazole-H), 5.56–6.23 (2H, ABq, 6,7-H's), 4.76 (2H, bs, 19-H's), 3.9–4.6 (2H, bm, 1,3-H's), 3.76 (3H, s, O—$CH_3$), 0.67 (3H, s, 18-H's).

b) 20α-[4-(2-Hydroxyprop-2-yl)-1,2,3-triazol-1-ylmethyl]-1α,3β-bis-triisopropylsilyloyx-9,10-secopregna-5(E), 7,10 (19)-triene [Formula (II) —A=(A-3), $R^1$=α-$CH_3$, $R^6$=$R^7$= (i-Pr)$_3$Si, W=$CH_2$, Y=valence bond, Z=4-C($CH_3$)$_2$OH]

The product from (a) above (75 mg) in ether (1 ml) was treated with methyl magnesium bromide (0.7 ml of a 2.1 M solution) and processed as in Example 5(b) to give the title compound (40 mg). UV (EtOH) $\lambda_{max}$268, $\lambda_{min}$233 nm$^{-1}$; IR (CDCl$_3$) $v_{max}$3600 cm$^{-1}$; NMR (CDCl$_3$) δ7.33 (1H, s, triazole-H), 5.73–6.46 (2H, ABq, 6,7-H's), 4.96 (2H, bs, 19-H's), 3.9–4.6 (2H, bm, 1,3-H's), 1.5 (s, gem di-Me), 0.6 (3H, s, 18-H's). ps c) 20α[4-(2-Hydroxyprop-2-yl)-1,2,3-triazol-1-ylmethyl]-1α,3β-bis-triisopropylsilyloxy-9,10- secopregna-5(Z),7,10(19)-triene [Formula (II) —A=(A-2), $R^1$=α-$CH_3$, $R^6$=$R^7$=(i-Pr)$_3$Si, W=$CH_2$, Y=valence bond, Z=4-C($CH_3$)$_2$OH]

A solution of the 5(E)-isomer from (b) above (33 mg) and phenazine (10 mg) in benzene (4.5 ml) was photoisomerised (1 hour) and worked up as in Example 5(c) to give the title compound (28 mg). UV (EtOH) $\lambda_{max}$261, $\lambda_{min}$230 nm; IR (CDCl$_3$) $\nu_{max}$3600 cm$^{-1}$; NMR (CDCl$_3$) δ7.3 (1H, s, triazole-H), 5.7–6.1 (2H, ABq, 6,7-H's), 4.93, 5.16 (each 1H, bs, 19-H's), 3.9–4.6 (2H, bm, 1,3-H's), 1.5 (s, gem di-Me), 0.6 (3H, s, 18-H's).

d) 1α,3β-Dihydroxy-20α-[4-(2-hydroxyprop-2-yl)-1,2,3-triazol-1-ylmethyl]-9,10-secopregna-5(Z),7,10(19)-triene [Formula (II) —A=(A-2), $R^1$=α-$CH_3$, $R^6$=$R^7$=H, W=$CH_2$, Y=valence bond, Z=4-C($CH_3$)$_2$OH]

The silyl ether from (c) above (28 mg) was deprotected with tetrabutylammonium fluoride (2 ml) in THF (1 ml) as in Example 5(d) to afford the title compound (12 mg). UV (EtOH) $\lambda_{max}$263, $\lambda_{min}$230 nm; IR (CDCl$_3$) $\nu_{max}$3580 cm$^{-1}$; NMR (CDCl$_3$) δ7.2 (1H, s, triazole-H), 5.96–6.13 (2H, ABq, 6,7-H's), 4.86, 5.16 (each 1H, bs, 19-H's), 1.73 (s, gem di-Me), 0.81 (d, 21-H's), 0.52 (3H, s, 18-H's).

EXAMPLE 8 a) 20(α,β)-(4-Methoxycarbonyl-1,2,3-triazol-1-ylmethyl)-1α,3β-bis-triisopropylsilyloxy-9,10-secopregna-5(E), 7,10 (19)-triene [Formula (II) —A=(A-3), $R^1$=α- and β-$CH_3$. $R^6$=$R^7$(i-Pr)$_3$Si, W=$CH_2$, Y=valence bond, Z=4-CO.O$CH_3$]

A mixture of the 20α- (normal) and 20β- (epi) azides prepared as in Example 3 (520 mg), methyl propiolate [Formula (IV) —Y=valence bond, Z'=CO.O$CH_3$] (5 ml) and benzene (2 ml) was stirred at room temperature for 72 hours and worked up as in Example 5(a) to give the title compounds (310 mg). UV (Et$_2$O) $\lambda_{max}$267, $\lambda_{min}$236 nm; IR (CCl$_4$) $\nu_{max}$1730 cm$^{-1}$; NMR (CCl$_4$) δ7.66 (1H, s, triazole-H), 5.4–6.06 (ABq, 6,7-H's), 4.66 (bs, 19-H's), 4.16–4.46 (bm, 1,3-H's), 3.6 (3H, s, O—$CH_3$), 0.5 and 0.56 (each s, 18-H's for normal and epi compounds).

b) 20(α,β)-[4-(3-Hydroxypent-3-yl)-1,2,3-triazol-1-ylmethyl]-1α,3β-bis-triisopropylsilyloxy-9,10-secopregna-5(E), 7,10(19)-triene [Formula (II) —A=(A-3) $R^1$=α- and β-$CH_3$, $R^6$32 $R^7$=(i-Pr)$_3$Si, W=$CH_2$,Y=valence bond, Z=4-C($C_2H_5$)$_2$OH]

The mixture of isomers from (a) above (120 mg) in THF (1 ml) was treated at 0° with ethyl magnesium bromide (0.54 ml of a 1M solution in THF). The reaction mixture was warmed to room temperature, stirred for 2 hours and then worked up and purified by chromatography to give the title compounds (80 mg). UV (Et$_2$O) $\lambda_{max}$267, $\lambda_{min}$231 nm; IR (CDCl$_3$) $\nu_{max}$3600–3400 cm$^{-1}$; NMR (CDCl$_3$) δ7.13 (1H, s, triazole-H), 5.56–6.26 (ABq, 6,7-H's), 4.8 (bs, 19-H's), 4.2–4.5 (bm, 1,3-H's), 0.6 (s, 18-H's).

The 20α- and 20β-isomers were separated by chromatography on silica gel developing with mixtures of ethyl acetate and hexane. The epi compound was the less polar (confirmed by chromatographic comparison with authentic normal compound made from pure 20α-azidomethyl compound). The NMR, IR and UV spectra were essentially identical.

c) 20β-[4-(3-Hydroxypent-3-yl)-1,2,3-triazol-1-ylmethyl]-1α,3β-bis-triisopropylsilyloxy-9,10-secopregna-5(Z),7,10 (19)-triene [Formula (II) —A=(A-2), $R^1$=β-$CH_3$, $R^6$=$R^7$=(i-Pr)$_3$Si, W=$CH_2$, Y=valence bond, Z=4-C($C_2H_5$)$_2$OH]

The 20β-(epi) compound from (b) above (28 mg) in benzene (4 ml) containing phenazine (20 mg) was photoisomerised and worked up as in Example 5(c) to give the title compound. UV (Et$_2$O) $\lambda^{max}$262, $\lambda_{min}$228 nm; IR (CHCl$_3$) $\nu_{max}$3600–3400 cm$^{-1}$; NMR (CCl$_4$) δ7.13 (1H, s, triazole-H), 5.73–6.26 (ABq, 6,7-H's), 4.53, 4.86 (each 1H, s, 19-H's), 0.5 (s, 18-H's).

d) 1α,3β-Dihydroxy-20β-[4-(3-hydroxypent-3-yl)-1,2,3-triazol-1-ylmethyl]-9,10-secopregna-5(Z),7,10(19)-triene [Formula (II) —A=(A-2), $R^1$=β-$CH_3$, $R^6$=$R^7$=H, W=$CH_2$, Y=valence bond, Z=4-C($C_2H_5$)$_2$OH]

The silyl ether from (c) above (14 mg) was desilyated with tetrabutylammonium fluoride (0.3 ml) as in Example 5(d) to afford the title compound (7 mg). UV (EtOH) $\lambda_{max}$263, $\lambda^{min}$228 nm; IR (CDCl$_3$) $\nu_{max}$3600–3400 cm$^{-1}$; NMR (CDCl$_3$) δ7.3 (1 H, s, triazole-H), 5.83–6.4 (ABq, 6,7-H's), 4.86, 5.26 (each 1H, s, 19-H's), 0.66–0.9 (m, 18-H's, Et-H's).

EXAMPLE 9 a) 20α-[4-(3-Hydroxypent-3-yl)-1,2,3-triazol-1-ylmethyl]-1α,3β-bis-triisopropylsilyloxy-9,10-secopregna-5(Z),7,10 (19)-triene [Formula (II) —A=(A-2), $R^1$=α-$CH_3$,$R^6$=$R^7$= (i-Pr)$_3$Si, W=$CH_2$, Y=valence bond, Z=4-C($CH_2H_5$)$_2$OH]

The 20α-(normal) compound from Example 8(b) above (80 mg) in benzene (11 ml) containing phenazine (40 mg) was photoisomerised and worked up as in Example 5(c) to give the title compound (50 mg). UV (Et$_2$O) $\lambda_{max}$262, $\lambda_{min}$229 nm; IR (CCl$_4$) $\nu_{max}$3600–3400 cm$^{-1}$; NMR (CCl$_4$) δ7.4 (1H, S, triazole-H), 5.73–6.26 (ABq, 6,7-H's), 4.33, 5.03 (each 1 H, s, 19-H's), 0.6 (s, 18-H's).

b) 1α,3β-Dihydroxy-20α[4-(3-hydroxypent-3-yl)-1,2,3-triazol-1-ylmethyl]-9,10-secopregna-5(Z),7,10(19)-triene [Formula (II) —A=(A-2), $R^1$=α-$CH_3$, $R^6$=$R^7$=H, W=$CH_2$, Y=valence bond, Z=4-C($C_2H_5$)$_2$OH]

The silyl ether from (a) above (50 mg) was desilyated with tetrabutylammonium fluoride (0.6 ml) as in Example 5(d) to afford the title compound (23 mg). UV (EtOH) $\lambda_{max}$263, $\lambda_{min}$227 nm; IR (CDCl$_3$) $\nu_{max}^{3600-3450}$ cm$^{-1}$; NMR (CDCl$_3$) δ7.23 (1H, s, triazole-H), 5.83–6.3 (ABq, 6,7-H's), 4.86, 5.26 (each 1H, s, 19-H's), 0.56–0.86 (m, Et-H's), 0.56 (s, 18-H's).

EXAMPLE 10 a) 20α-(4-N,N-Pentamethylenecarbamoyl-1,2,3-triazol-1-ylmethyl]-1α,3β-bis-triisopropylsilyloxy-9,10-secopregna-5(E), 7,10(19)-triene [Formula (II) —A=(A-3), $R^1$=α-$CH_3$, $R^6$=$R^7$=(i-Pr)$_3$Si, W=$CH_2$, Y=valence bond, Z=4-CO.N$R^2R^3$ where $R^2+R^3$=($CH_2$)$_5$]

A solution of 20α-(4-methoxycarbonyl-1,2,3-triazol-1-ylmethyl)-1α,3β-bis-triisopropylsilyloxy-9,10-secopregna-5(E), 7,10(19)-triene prepared as in Example 7(a) (150 mg) in hexane (1 ml) was treated at −78° with piperidine (0.56 ml) and [(Me$_3$Si)$_2$N]$_2$Sn (putatively 0.8 m mole in hexane) and then allowed to warm to room temperature. After 1.5 hours only ca. 60% of the starting material had been consumed so the reaction mixture was cooled to −78°, further tin reagent and piperidine were added (ca. 0.2 m mole each), and the mixture allowed to warm to room temperature. After an hour (starting material gone) the reaction was worked up and the product purified by TLC to give the title compound (165 mg). UV (Et$_2$O) $\lambda_{max}$267, $\lambda_{min}$237 nm; IR (CCl$_4$) $\nu_{max}$1630 cm$^{-1}$; NMR (CCl$_4$) δ8.13 (1H, s, triazole-H), 5.66–6.46 (2H, ABq, 6,7-H's), 4.9 (2H, bs, 19-H's), 3.6–4.3 (bm, 1,3-H's), 4.2–4.3 (nm, N—$C_2$'s), 0.63 (3H, s, 18-H's)

b) 20α-(4-N,N-Pentamethylenecarbamoyl-1,2,3-triazol-1-ylmethyl]-1α,3β-bis-triisopropylsilyloxy-9,10-secopregna-5(Z),7,10(19)-triene [Formula (II) —A=(A-2), $R^1$=α-$CH_3$, $R^6$=$R^7$=(i-Pr)$_3$Si, W=$CH_2$, Y=valence bond, Z=4-CO.N$R^2R^3$ where $R^2+R^3$=($CH_2$)$_5$]

A solution of the 5(E)-isomer from (a) above (165 mg) in benzene (20 ml) containing phenazine (77 mg) was photoisomerized (1.75 hours) as in Example 5(c) to give the title compound (120 mg, isolated by column chromatography followed by TLC). IR (CCl$_4$) $v_{max}$1620 cm$^{-1}$; NMR (CCl$_4$) δ7.86 (1H, s, triazole-H), 5.6–6.2 (2H, ABq, 6,7-H's), 4.66 and 5.06 (2s, 19-H's), 3.53–4.2 (bm, 1,3-H's), 4.1 (nm, N—CH$_2$'s), 0.56 (3H, s, 18-H's).

c) 1α,3β-Dihydroxy-20α-[4-N,N-pentamethylenecarbamoyl-1,2,3-triazol-1-ylmethyl]-9,10-secopregna-5(Z),7,10(19)-triene [Formula (II) —A=(A-2), R$^1$=α-CH$_3$- R$^6$=R$^7$=H, W=CH$_2$, Y=valence bond, Z=4-CO.NR$^2$R$^3$ where R$^2$+R$^3$ (CH$_2$)$_5$]

The silyl ether from (b) above (80 mg) was desilylated with tetrabutylammonium fluoride as in Example 5(d) to give (after chromatography) the title compound (13 mg). IR (CDCl$_3$) $v_{max}$3350–3600, 1610 cm$^{-1}$; NMR (CDCl$_3$) δ7.8 (1H, S, triazoline-H), 5.76–6.3 (2H, ABq, 6,7-H's), 4.86 and 5.2 (2s, 19-H's), 3.53–4 (bm, 1,3-H's), 4–4.23 (nm, N—CH$_3$'s), 0.85 (d, 21-H's), 0.56 (3H, s, 18-H's).

By repeating the procedures of (a)–(c) above using different amines in place of piperidine in step (a) the following compounds are obtained:

20α-[4-(N,N-diethylcarbamoyl)-1,2,3-triazol-1-ylmethyl]-1α,3β-dihydroxy-9,10-secopregna-5(Z) 7,10 (19)-triene [Formula (II) —A =(A-2), R$^1$=α-CH$_3$, R$^6$=R$^7$=H, W=CH$_2$, Y=valence bond, Z=4-CO.NR$^2$R$^3$ where R$^2$=R$^3$=C$_2$H$_5$], using diethylamine as amine;

20α-[4-(N-cyclopropylcarbamoyl)-1,2,3-triazol-1-ylmethyl]- 1α,3β-dihydroxy-9,10-secopregna-5(Z),7,10 (19)-triene [Formula (II) —A =(A-2), R$^1$=α-CH$_3$, R$^6$=R$^7$=H, W=CH$_2$, Y=valence bond, Z=4-CO.NR$^2$R$^3$ where R$^2$=H, R$^3$=cyclopropyl], using cyclopropylamine as amine;

20α-[4-(N,N-3-oxapentamethylenecarbamoyl)-1,2,3-triazol-1-ylmethyl]-1α,3β-dihydroxy-9,10-secopregna-5 (Z),7,10(19)-triene [Formula (II) —A=(A-2), R$^1$=α-CH$_3$, R$^6$=R$^7$=H, W=CH$_2$, Y=valence bond, Z=4-CO.NR$^2$R$^3$ where R$^2$+R$^3$=(CH$_2$)$_2$.O. (CH$_2$)$_2$], using morpholine as amine; and 20α-[4-(N,N-diisopropylcarbamoyl)-1,2,3-triazol-1-ylmethyl]-1α,3β-dihydroxy-9,10-secopregna-5(Z),7,10 (19)-triene [Formula (II) —A=(A-2), R$^1$=α-CH$_3$, R$^6$=R$^7$=H, W=CH$_2$, Y=valence bond, Z=4-CO.NR$^2$R$^3$ where R$^2$=R$^3$=i-C$_3$H$_7$], using diisopropylamine as amine.

By repeating the procedures of (a)–(c) above starting from the corresponding 20β-diastereomer the compound 20β-[4-(N,N-pentamethylenecarbamoyl)-1,2,3-triazol-1-ylmethyl]-1α,3β-dihydroxy-9,10-secopregna-5(Z),7,10(19)-triene [Formula (II) —A=(A-2), R$^1$=β-CH$_3$, R$^6$=R$^7$=H, W=CH$_2$, Y=valence bond, Z=4-CO.NR$^2$R$^3$ where R$^2$=R$^3$=(CH$_2$)$_5$] is obtained.

Starting from this 20β-diastereomer and using different amines in place of piperidine in step (a) the following compounds are obtained:

20β-[4-(N,N-diethylcarbamoyl)-1,2,3-triazol-1-ylmethyl]-1α,3β-dihydroxy-9,10-secopregna-5(Z),7,10 (19)-triene [Formula (II) —A=(A-2), R$^1$=β-CH$_3$, R$^6$=R$^7$= H, W=CH$_2$, Y=valence bond, Z=4-CO.NR$^2$R$^3$ where R$^2$=R$^3$=C$_2$H$_5$], using diethylamine as amine;

20β-[4-(N-cyclopropylcarbamoyl)-1,2,3-triazol-1-ylmethyl]-1α,3β-dihydroxy-9,10-secopregna-5(Z),7,10 (19)-triene [Formula (II) —A=(A-2), R$^1$=β-CH$_3$, R$^6$=R$^7$=H, W=CH$_2$, Y=valence bond, Z=4-CO.NR$^2$R$^3$ where R$^2$=H, R$^3$=cyclopropyl], using cyclopropylamine as amine;

20β-[4-(N,N-3-oxapentamethylenecarbamoyl)-1,2,3-triazol-1-ylmethyl]-1α,3β-dihydroxy-9,10-secopregna-5 (Z),7,10(19)-triene [Formula (II) —A=(A-2), R$^1$=βCH$_3$, R$^6$=R$^7$=H, W=CH$_2$, Y=valence bond, Z=4-CO.NR$^2$R$^3$ where R$^2$+R$^3$=(CH$_2$)$_2$.O. (CH$_2$)$_2$], using morpholine as amine; and 20β-[4-(N,N-diisopropylcarbamoyl)-1,2,3-triazol-1-ylmethyl]-1α,3βD-dihydroxy-9,10-secopregna-5(Z),7,10 (19)-triene [Formula (II) —A=(A-2), R$^1$=β-CH$_3$, R$^6$=R$^7$=H, W=CH$_2$, Y=valence bond, Z=4-CO.NR$^2$R$^3$ where R$^2$=R$^3$=i-C$_3$H$_7$], using diisopropylamine as amine.

By repeating the procedures of (a)–(c) above starting from 20α-[2-(4-methoxycarbonyl-1,2,3-triazol-1-yl)ethyl]-1α, 3β-bis-triisopropylsilyloxy-9,10-secopregna-5(E), 7,10(19)-triene [Formula (II) —A=(A-3), R$^1$=α-CH$_3$, R$^6$=R$^7$=(i-Pr)$_3$Si, W=(CH$_2$)$_2$, Y=valence bond, Z=4-CO$_2$CH$_3$] the compound 20α-{2-[4-(N,N-pentamethylenecarbamoyl)-1,2, 3-triazol-1-yl]ethyl}-1α,3β-dihydroxy-9,10-secopregna-5 (Z),7,10(19)-triene [Formula (II) —A=(A-2), R$^1$=α-CH$_3$, R$^6$=R$^7$=H, W=(CH$_2$)$_2$, Y=valence bond, Z=4-CO.NR$^2$R$^3$ where R$^2$+R$^3$=(CH$_2$)$_5$] is obtained.

Starting from this 20α-triazolylethyl compound and using different amines in place of piperidine in step (a) the following compounds are obtained:

20α-{2-[4-(N,N-diethylcarbamoyl)-1,2,3-triazol-1-yl] ethyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_2$, Y=valence bond, Z=4-CO.NR$^2$R$^3$ where R$^2$=R$^3$=C$_2$H$_5$], using diethylamine as amine;

20α-{2-[4-(N-cyclopropylcarbamoyl)-1,2,3-triazol-1-yl] ethyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_2$ Y=valence bond, Z=4-CO.NR$^2$R$^3$ where R$^2$H, R$^3$=cyclopropyl], using cyclopropylamine as amine;

20α-{2-[4-(N,N-3-oxapentamethylenecarbamoyl)-1,2,3-triazol-1-yl]ethyl}-1α,3β-dihydroxy-9,10-secopregna-5(Z), 7,10(19)-triene [Formula (II) —A=(A-2), R$^1$=α-CH$_3$, R$^6$=R$^7$=H, W=(CH$_2$)$_2$, Y=valence bond, Z=4-CO.NR$^2$R$^3$ where R$^2$+R$^3$=(CH$_2$)$_2$.O. (CH$_2$)$_2$], using morpholine as amine; and 20α-{2-[4-(N,N-diisopropylcarbamoyl)-1,2,3-triazol-5-yl]ethyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_2$, Y=valence bond, Z=4-CO.NR$^2$R$^3$ where R$^2$=R$^3$=i-C$_3$H$_7$], using diisopropylamine as amine.

EXAMPLE 11 a) 20α-[4-(1-Hydroxycyclohex-1-yl)-1,2,3-triazol-1-ylmethyl]-1α,3β-bis-triisopropylsilyloxy-9,10-secopregna-5(E), 7,10(19)-triene [Formula (I1) —A=(A-3). R$^1$=α-CH$_3$, R$^6$=R$^7$=(i-Pr)$_3$Si, W=$_2$, Y=valence bond. Z=4-C(R$^4$)(R$^5$) .OH where R$^4$+R$^5$=(CH$_{25}$]

The 20α-azidomethyl compound from Example 2 (100 mg), 1-ethynylcyclohexan-1-ol and a few drops of water were heated at 95° with stirring for 15 hours. The crude product was dissolved in ether, washed with water, concentrated and purified by chromatography on silica gel. Elution with 10% ethyl acetate in hexane first gave a mixture of the major and minor isomers (20 mg) followed by the major isomer, the title compound (49 mg). UV (Et$_2$O) $\lambda_{max}$267, $\lambda_{min}$232 nm; NMR (CDCl$_3$) δ7.16 (s, triazole H), 5.6–6.38 (AB q, 6,7-H's), 4.86 (bs, 19-H's), 0.6 (s, 18-H's).

b) 20-[4-(1-Hydroxycyclohex-1-yl)-1,2,3-triazol-1-ylmethyl]-1α,3β-bis-triisopropylsilyloxy-9,10-secopregna-5(Z),7,10(19)-triene [Formula (II) —A=(A-2). R$^1$=α-CH$_3$, R$^6$=R$^7$=(i-Pr)$_3$Si, W=CH$_2$, Y=valence bond, Z=4-C(R$^4$) (R$^5$) OH where R$^4$+R$^5$=(CH$_2$)$_5$]

The 5(E) triazole from (a) above (35 mg) was photoisomerised as in Example 1(b) using phenazine (15 mg) in benzene (4 ml) The title compound (25 mg) was isolated by chromatography. UV (Et$_2$O) $\lambda_{max}$262, $\lambda_{min}$230 nm; NMR (CDCl$_3$) δ7.23 (s, triazole H), 5.7–6.3 (AB q, 6,7-H's), 4.8, 5.13 (ea s, 19-H's), 3.9–4.46 (bm, 1,3-H's), 0.56 (s, 18-H's).

c) 20α-[4-(1-Hydroxycyclohex-1-yl)-1,2,3-triazol-1-ylmethyl]-1α,3β-dihydroxy-9,10-secopregna-5(Z),7,10(19)-triene [Formula (II) —A=(A-2). R$^1$=α-CH$_3$, R$^6$=R$^7$=H, W=CH$_2$, Y=valence bond, Z=4-C(R$^4$)(R).OH where R$^4$+R$^5$=(CH$_2$)$_5$]

The silyl ether from (b) above (25 mg) in THF (0.2 ml) was desilylated as in Example 1(c) using a solution of tetrabutylammonium fluoride in THF (0.2 ml, 1.0M). The title compound (6.6 mg) was isolated by chromatography. UV (EtOH) λ$_{max}$263, λ$_{min}$230 nm; NMR (CDCl$_3$) δ7.23 (s, triazole H), 5.76–6.36 (AB q, 6,7-H's), 4.9, 5.2 (ea s, 19-H's), 4.0–4.4 (bm, 1,3-H's), 1.23 (s, cyclic CH$_2$'s), 0.81 (d, 21-H's), 0.56 (s, 18-H's).

EXAMPLE 12 a) 2α-(2-Azidoethyl)-1α,3β-bis-triisopropylsilyloxy-9,10-secopregna-5(E),7,10(19)-triene [Formula (I) —A=(A-3), R$^1$=α-CH$_3$, R$^6$=R$^7$=(i-Pr)$_3$Si, W=(CH$_2$)$_2$, X=N$_3$]

A solution of the corresponding 20α-hydroxyethyl compound (200 mg) prepared as in Preparation 6 and 1,8-bis-dimethylaminonaphthalene (185 mg) in methylene chloride (1 ml) was cooled to −50°, treated with trifluoromethane-sulphonic anhydride (0.072 ml), returned to room temperature and stirred for 1 hour. The mixture was then treated with a solution of sodium azide (195 mg) and tetrabutylammonium bromide (8 mg) in water (4 ml), and then stirred at room temperature for 1 hour. Following workup, the title compound (202 mg) was isolated by column chromatography. UV (Et$_2$O) λ$_{max}$267, λ$_{min}$228 nm; IR (CCl$_4$) ν$_{max}$2100 cm$^{-1}$ (N$_3$)$_3$; NMR (CCl$_4$) δ5.46–6.23 (AB q, 6,7-H's), 4.76, (bs, 19-H's), 0.56 (s, 18-H's).

b) 20α-[2-(4-Methoxycarbonyl-1,2,3-triazol-1-yl)ethyl]-1α,3β-bis-triisopropylsilyloxy-9,10-secopregna-5(E), 7,10(19)-triene [Formula (II) —A=(A-3), R$^1$=α-CH$_3$, R$^6$=R$^7$=(i-Pr)$_3$Si, W=(CH$_2$)$_2$, Y=valence bond, Z=4-CO$_2$CH$_3$]

A mixture of the azide from (a) above (202 mg), methyl propiolate (1.5 ml) and benzene (0.5 ml) was stirred at room temperature for 48 hours, concentrated in vacuo, and the product was purified by chromatography to give the title compound (72 mg, major isomer). UV (Et$_2$O) λ$_{max}$266,267, λ$_{min}$237 nm; IR (CDCl$_3$) ν$_{max}$1730 cm$^{-1}$ (ester); NMR (CDCl$_3$) δ7.03 (s, triazole H), 5.53–6.3 (AB q, 6,7-H's), 4.83, (bs, 19-H's), 4.03–4.46 (m, 1,3-H's), 3.8 (s, CO$_2$CH$_3$) 0.5 (s, 18-H's).

c) 20α-2-[4-(3-Hydroxypent-3-yl)-1,2,3-triazol-1-yl]ethyl-1α,3β-bis -triisopropylsilyloxy-9,10-secopregna-5(E), 7,10(19)-triene [Formula (II) —A=(A-3), R$^1$=α-CH$_3$, R$^6$=R$^7$=(i-Pr)$_3$Si, W=(CH$_2$)$_2$, Y=valence bond, Z=4-C(C$_2$H$_5$)$_2$OH]

A solution of the ester from (b) above (70 mg) in ether (1 ml) was cooled to 0° and treated with ethyl magnesium bromide (0.2 ml of a 3M solution). The reaction mixture was warmed to room temperature, kept at that temperature for 2 hours, cooled to 0° and treated with excess saturated ammonium chloride solution. The product was extracted into ether and purified by chromatography to give the title compound (53 mg) UV (Et$_2$O) λ$_{max}$266,267, λ$_{min}$233 nm; IR (CDCl$_3$) ν$_{max}$3600 cm$^{-1}$ (OH); NMR (CDCl$_3$) δ7.2 (s, triazole H), 5.6–6.4 (AB q, 6,7-H's), 4.86, (bs, 19-H's), 4.0–4.46 (m, 1,3-H's), 0.46 (s, 18-H's).

d) 20α-2-[4-(3-Hydroxypent-3-yl)-1,2,3-triazol-1-yl]ethyl-1α,3β-bis-triisopropylsilyloxy-9,10-secopregna-5(Z),7,10(19)-triene [Formula (II) —A (A-2), R$^1$=α-CH$_3$, R$^6$=R$^7$=(i-PR)$_3$Si, W=(CH$_2$)$_2$, Y=valence bond, Z=4-C(C$_2$H$_5$)$_2$OH]

A solution of the 5(E) triene from (c) above (53 mg) was photoisomerised as in Example 1(b) using phenazine (20 mg) in benzene (6 ml). The title compound (22.2 mg) was isolated by chromatography. UV (Et$_2$O) λ$_{max}$260,261, λ$_{min}$228 nm; IR (CDCl$_3$) ν$_{max}$3550 cm$^{-1}$ (OH); NMR (CDCl$_3$) δ7.0 (s, triazole H), 5.6–6.1 (AB q, 6,7-H's), 4.7, 5.3 (ea s, 19-H's), 0.5 (s, 18-H's)

e) 20α-2-[4-(3-Hydroxypent-3-yl)-1,2,3-triazol-1-yl]ethyl-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_2$, Y=valence bond, Z=4-C(C$_2$H$_5$)$_2$OH]

The silyl ether from (d) above (22 mg) in THF (0.5 ml) was desilylated as in Example 1(c) using a solution of tetrabutylammonium fluoride in THF (0.4, ml, 1.0 M) for 2.5 hours. The title compound (10.8 mg was isolated by chromatography. UV (EtOH) λ$_{max}$262, λ$_{min}$228,229 nm; IR (CDCl$_3$) ν$_{max}$3600 cm$^{-1}$ (OH); NMR (CDCl$_3$) δ7.0 (s, triazole H), 5.6–6.16 (AB q, 6,7-H's), 4.7, 5.06 (ea s, 19-H's), 3.83–4.36 (m, 1,3-H's), 1.6–1.83 (m, CH$_2$CH$_3$), 0.63–0.96 (m, 21-H's, CH$_3$CH$_2$), 0.46 (s, 18-H's).

EXAMPLE 13 a) 20β-(2-Azidoethyl)-1α,3β-bis-triisoproplsilyloxy-9,10-secopregna-5(E), 7,10(19)-triene [Formula (1) —A=(A-3), R$^1$=β-CH$_3$, R$^6$=R$^7$=(i-Pr )$_3$Si, W=(CH$_2$)$_2$, X=N$_3$]

A solution of the corresponding 20β-hydroxyethyl compound (252 mg) prepared as in Preparation 6 and 1,8-bis-dimethylaminonaphthalene (260 mg) in methylene chloride (3.75 ml) was cooled to −70°, treated with trifluoromethane-sulphonic anhydride (0.1 ml), returned to room temperature and stirred for 1 hour. The mixture was then cooled to 0°, treated with a solution of sodium azide (243 mg) and tetrabutylammonium bromide (10 mg) in water (5 ml), and then stirred at room temperature for 30 minutes. Following workup, the title compound (276 mg) was isolated by column chromatography. UV (Et$_2$O) λ$_{max}$268, λ$_{min}$228 nm; IR (CCl$_4$) ν$_{max}$2100 cm$^{-1}$ (N$_3$); NMR (CCl$_4$) δ5.46–6.23 (AB q, 6,7-H's), 4.76 (bs, 19-H's), 0.56 (s, 18-H's). ps b) 20β-2-[4-(3-Hydroxypent-3-yl)-1,2,3-triazol-1-yl]-ethyl-1α,3β-bis-triisopropylsilyloxy-9,0-secopregna-5(E), 7,10 (19)-triene [Formula (II) —A=(A-3), R$^1$=β-CH$_3$, R$^6$=R$^7$=(i-Pr)$_3$Si, W=(CH$_2$)$_2$, Y=valence bond, Z=4-C(C$_2$H$_5$)OH]

A mixture of the azide from (a) above (120 mg), 3-ethylpent-1-yn-3-ol (566 mg) and a few drops of water was heated at 90° for 20 hours, concentrated in vacuo, and the product was purified by chromatography to give the title compound (49 mg, major isomer). UV (Et$_2$O) λ$_{max}$268, λ$_{min}$232 nm; IR (CDCl$_3$) ν$_{max}$3600 (OH); NMR (CDCl$_4$) δ7.2 (s, triazole H), 5.6–6.33 (AB q, 6,7-H's), 4.83 (bs, 19-H's), 4.0–4.4 (m, 1,3-H's), 0.5 (s, 18-H's).

c) 20β-2-[4-(3-Hydroxypent-3-yl)-1,2,3-triazol-1-yl]-ethyl-1α,3β-bis-triisopropylsilyloxy-9,10-secopregna-5(Z),7,10(19)-triene [Formula (II) —A=(A-2), R$^1$=β-CH$_3$, R$^6$=R$^7$=(i-Pr)$_3$Si,W=(CH$_2$)$_2$, Y=valence bond, Z=4-C(C$_2$H$_5$)$_2$OH]

A solution of the 5(E)-triene from (b) above (52 mg) was photoisomerised as in Example 1(b) using phenazine (20 mg) in benzene (6 ml) The title compound (42 mg) was isolated by chromatography. UV (Et$_2$O) λ$_{max}$263,262, λ$_{min}$231 nm; IR (CDCl$_3$) ν$_{max}$3550 cm$^{-1}$ (OH); NMR (CDCl$_3$) δ7.23 (s, triazole H), 5.76–6.33 (AB q, 6,7-H's), 4.8, 5.13 (ea s, 19-H's), 4.13–4.5 (bm, 1,3-H's), 0.46 (s, 18-H's).

d) 20β-2-[4-(3-Hydroxypent-3-yl)-1,2,3-triazol-1-yl]-ethyl-1α,3β-dihydroxy-9,10-secopregna-5(Z),7,10(19)-triene [Formula (II) —A=(A-2), R$^1$=-β-CH$_3$, R$^6$=R$^7$=H, W=(CH$_2$)$_2$, Y=valence bond, Z=4-C(C$_2$H$_5$)$_2$OH]

The silyl ether from (c) above (42 mg) in THF (1 ml) was desilylated as in Example 1(c) using a solution of tetrabutylammonium fluoride in THF (0.8 ml, 1.0M) for 3 hours. The title compound (22 mg) was isolated by chromatography. UV (EtOH) λ$_{max}$263,264, λ$_{min}$229 nm; IR (CDCl$_3$)

$v_{max}$3600 cm$^{-1}$ (OH); NMR (CDCl$_3$) δ7.13 (s, triazole H), 5.57–6.26 (AB q, 6,7-H's), 4.8, 5.13 (ea s, 19-H's), 0.46 (s, 18-H's).

The compound 20α-{3-[4-(3-hydroxypent-3-yl)-1,2,3-triazol-1-yl]propyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_3$, Y=valence bond, Z=4-C(R$^4$)(R$^5$).OH where R$^4$=R$^5$=C$_2$H$_5$] is prepared by reacting the product of Example 1(a) in accordance with (b)–(d) above.

By repeating this procedure starting from the product of Example 1(a) and using different alkynes in step (b) the following compounds are obtained:

20α-{3-[4-(3-methyl-3-hydroxybutyl)-1,2,3-triazol-1-yl]propyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_3$, Y=(CH$_2$)$_2$, Z=4-C(R$^4$)(R$^5$).OH where R$^4$=R$^5$=CH$_3$], using 5-methylhex-1-yn-5-ol as alkyne;

20α-{3-[4-(2-methyl-2-hydroxypentyl)-1,2,3-triazol-1-yl]propyl}-1α,3β-dihydroxy-9,10-secopregna-5(Z),7,10(19)-triene [Formula (II) —A=(A-2), R$^1$=αCH$_3$, R$^6$=R$^7$=H, W=(CH$_2$)$_3$, Y=CH$_2$, Z=4-C(R$^4$)(R$^5$).OH where R$^4$=n-C$_3$H$_7$, R$^5$=CH$_3$], using 4-methylhept-1-yn-4-ol as alkyne;

20α-{3-[4-(4-ethyl-4-hydroxyhexyl)-1,2,3-triazol-1-yl]propyl}-1α,3β-dihydroxy-9,10-secopregna-5(Z),7,10(19)-triene [Formula (II) —A=(A-2), R$^1$αCH$_3$, R$^6$=R$^7$=H, W=(CH$_2$)$_3$, Y=(CH$_2$)$_3$, Z=4-C(R$^4$)(R$^5$).OH where R$^4$=R$^5$=C$_2$H$_5$], using 6-ethyloct-1-yn-6-ol as alkyne;

20α-{3-[4-(2-hydroxybut-2-yl)-1,2,3-triazol-1-yl]propyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_3$, Y=valence bond, Z=4-C(R$^4$)(R$^5$).OH where R$^4$=C$_2$H$_5$, R$^5$=CH$_3$], using 3-methylpent-1-yn-3-ol as alkyne;

20α-{3-[4-(4-methyl-2-hydroxypent-2-yl)-1,2,3-triazol-1-yl]propyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_3$, Y=valence bond, Z=4-C(R$^4$)(R$^5$).OH where R$^4$=i-C$_4$H$_9$, R$^5$=CH$_3$], using 3,5-dimethylhex-1-yn-3-ol as alkyne; and 20α-{3-[4-(2,4-dimethyl-3-hydroxypent-3-yl)-1,2,3-triazol-1-yl]propyl}-1α,3β-dihydroxy-9,10-secopregna-5(Z),7,10(19)-triene [Formula (II) —A=(A-2), R$^1$=α-CH$_3$, R$^6$=R$^7$=H, W=(CH$_2$)$_3$, Y=valence bond, Z=4-C(R$^4$)(R$^5$).OH where R$^4$=R$^5$=i-C$_3$H$_7$], using 2,4-dimethyl-3-ethynylpentan-3-ol as alkyne

EXAMPLE 14 a) 20α-[4-(2-Ethyl-2-hydroxbutyl)-1,2,3-triazol-1-ylmethyl]-1α,3β-bis-triisopropylsilyloxy-9,10-secopregna-5(E), 7,10(19)-triene [Formula (II) —A=(A-3), R$^1$=α-CH$_3$, R$^6$=R$^7$=(i-Pr)$_3$Si, W=CH$_2$, Y=CH$_2$, Z=4-C(R$^4$)(R$^5$)OH where R$^4$=R$^5$=C$_2$H$_5$] and 20α-[5-(2-ethyl-2-hydroxybutyl)-1,2,3-triazol-1-ylmethyl]-1α,3β-bis-triisopropylsilyloxy-9,10-secopregna-5 (E), 7,10(19)-triene [Formula (II) —A=(A-3), R$^1$=α-CH$_3$, R$^6$=R$^7$=(i-Pr)$_3$Si, W=CH$_2$, Y=CH$_2$, Z=5-C(R$^4$)(R$^5$)OH where R$^4$=R$^5$=C$_2$H$_5$]

The 20α-azidomethyl compound from Example 2 (100 mg), 3-ethylhex-5-yn-3-ol [Formula (IV), Y=CH$_2$, Z'=—C(R$^4$)(R$^5$).(OH) where R$^4$=R$^5$=C$_2$H$_5$) (320 mg) and a few drops of water were heated at 95° with stirring for 22 hours. The crude product was dissolved in ether, washed with water, concentrated and purified by chromatography on silica gel. Elution with 15% ethyl acetate in hexane first gave the major isomer, presumed to be the 4-substituted title compound (49 mg). UV (Et$_2$O) $\lambda_{max}$267, $\lambda_{min}$231,232 nm; NMR (CDCl$_3$) δ7.26 (s, triazole H), 5.36–6.46 (AB q, 6,7-H's), 4.9 (bs, 19-H's), 4.03–4.33 (m, 1,3-H's), 2.8 (s, CH$_2$ next to triazole), 0.6 (s, 18-H's). This was followed by the minor isomer, presumed to be the 5-substituted title compound (22 mg). UV (Et$_2$O) $\lambda_{max}$272, $\lambda_{min}$229 nm; NMR (CDCl$_3$) δ7.5 (s, triazole H), 5.66–6.5 (AB q, 6,7-H's), 4.9 (bs, 19-H's), 4.13–4.6 (m, 1,3-H's), 2.76 (s, CH$_2$ next to triazole), 0.6 (s, 18-H's)

b) 20α-4-(2-Ethyl-2-hydroxybutyl)-1,2,3-triazol-1-ylmethyl]-1α,3β-bis-triisopropylsilyloxy-9,10-secopregna-5(Z),7,10(19)-triene [Formula (II) —A=(A-2), R$^1$=α-CH$_3$, R$^6$=R$^7$=(i-Pr)$_3$Si, W=CH$_2$, Y=CH$_2$, Z=4-C(R$^4$)(R$^5$).OH where R$^4$=R$^5$=C$_2$H$_5$]

The 5(E) major triazole from (a) above (32 mg) was photoisomerised as in Example 1(b) using phenazine (17 mg) in benzene (5 ml). The title compound (25 mg) was isolated by chromatography. UV (Et$_2$O) $\lambda_{max}$263, $\lambda_{min}$228 nm; NMR (CDCl$_3$) δ7.23 (s, triazole H), 5.7–6.4 (AB q, 6,7-H's), 4.83, 5.13 (ea s, 19-H's), 3.93–4.4 (bm, 1,3-H's), 2.8 (s, CH$_2$ next to triazole), 0.56 (s, 18-H's)

c) 20α-[4-(2-Ethyl-2-hydroxybutyl)-1,2,3-triazol-1-ylmethyl]-1α,3ββ-dihydroxy-9,10-secopregna-5(Z),7,10(19)-triene [Formula (II) —A=(A-2), R$^1$=α-CH$_3$, R$^6$=R$^7$=H, W=CH$_2$, Y=CH$_2$, Z=4-C(R$^4$)(R$^5$).OH where R$^4$=R$^5$=C$_2$H$_5$]

The silyl ether from (b) above (26 mg) in THF (0.3 ml) was desilylated as in Example 1(c) using a solution of tetrabutylammonium fluoride in THF (0.3 ml, 1.0M) at room temperature overnight. The title product (11.2 mg) was isolated by chromatography. UV (EtOH) $\lambda_{max}$263, $\lambda_{max}$231 nm; NMR (CDCl$_3$) δ7.26 (s, triazole H), 5.86–6.43 (AB q, 6,7-H's), 4.93, 5.23 (ea s, 19-H's), 3.8–4.4 (bm, 1,3-H's), 1.23–1.56 (m, OH, CH$_2$CH$_3$), 0.8–0.96 (m, 21-H's, CH$_3$CH$_2$), 0.6 (s, 18-H's).

d) 20α-[5-(2-Ethyl-2-hydroxybutyl)-1,2,3-triazol-1-ylmethyl]-1α,3β-bis-triisopropylsilyloxy-9,10-secopregna-5(Z),7,10(19)-triene Formula (II) —A=(A-2), R$^1$=α-CH$_3$, R$^6$=R$^7$=(i-Pr)$_3$Si, W=CH$_2$, Y=CH$_2$, Z=5-C(R$^4$)(R$^5$).OH where R$^4$=R$^5$=C$_2$H$_5$]

The 5(E) minor triazole from (a) above (22 mg) was photoisomerised as in Example 1(b) using phenazine (20 mg) in benzene (4.5 ml). The title compound (17.5 mg) was isolated by chromatography. UV (Et$_2$O) $\lambda_{max}$261, $\lambda_{min}$229 nm; NMR (CDCl$_3$) δ7.43 (s, triazole H), 5.7–6.36 (AB q, 6,7-H's), 4.8, 5.2 (ea s, 19-H's), 3.96–4.56 (bm, 1,3-H's), 2.7 (d, CH$_2$ next to triazole), 0.56 (s, 18-H's).

e) 20α-[5-(2-Ethyl-2-hydroxybutyl)-1,2,3-triazol-1-ylmethyl]-1α,3β-dihydroxy-9,10-secopregna-5(Z),7,10(19)-triene [Formula (II) —A=(A-2), R$^1$=α-CH$_3$, R$^6$=R$^7$=H, W=CH$_2$, Y=CH$_2$, Z=5-C(R$^4$)(R$^5$).OH where R$^4$=R$^5$=C$_2$H$_5$]

The silyl ether from (d) above (17 mg) in THF (0.2 ml) was desilylated as in Example 1(c) using a solution of tetrabutylammonium fluoride in THF (0.2 ml, 1.0M) at room temperature overnight. The title product (7.2 mg) was isolated by chromatography. UV (EtOH) $\lambda_{max}$262, $\lambda_{min}$230 nm; NMR (CDCl$_3$) δ7.4 (s, triazole H), 5.73–6.5 (AB q, 6,7-H's), 4.93, 5.23 (ea s, 19-H's), 3.93–4.44 (bm, 1,3-H's), 2.73 (s, C$\underline{H}_2$ next to triazole), 1.4–1.66 (m, CH$_2$CH$_3$), 1.23 (s, OH), 0.7–1.0 (m, 21-H's, C$\underline{H}_3$CH$_2$), 0.6 (s, 18-H's).

Following the above procedures:

the compound 20α-azidomethyl-1α,3β-bis-triisorpropylsilyloxy-9,10-secopregna-5(E), 7-diene [Formula (I)-A=(A-5), R$^1$=α-CH$_3$, R$^6$=R$^7$=(i-Pr)$_3$Si, W=CH$_2$, X=N$_3$] is converted into 20α-4-(3-hydroxypent-3-yl)-1,2,3-triazol-1-ylmethyl-1α,3β-dihydroxy-9,10-secopregna-5(E), 7-diene [Formula (II) —A =(A-5), R$^1$=α-CH$_3$, R$^6$=R$^7$=H, W=CH$_2$, Y=valence bond, Z=4-C(R$^4$)(R$^5$).OH where R$^4$=R$^5$=C$_2$H$_5$];

the compound 20α-azidomethyl-1α,3β-bis-triisopropylsilyloxy-9,10-secopregna-5(Z), 7-diene [Formula (I) —A=(A-4), R=α-$CH_3$, $R^6$=$R^7$=(i-Pr)$_3$ Si, W=$CH_2$, X=$N_3$] is converted into 20α-4-(3-hydroxypent- 3-yl)-1,2,3-triazol-1-ylmethyl-1α,3β-dihydroxy-9,10-secopregna-5(Z), 7-diene [Formula (II) —A =(A-4), $R^1$=α-$CH_3$, $R^6$=$R^7$=H, W=$CH_2$, Y=valence bond, Z=4-C($R^4$)($R^5$).OH where $R^4$=$R^5$=$C_2H_5$];

the compound 20α-azidomethyl-1α,3β-bis-triisopropylsilyloxy-10-spirocyclopropyl-9,10-secopregna-5(E), 7-diene [Formula (I) —A=(A-7), $R^1$=α-$CH_3$, $R^6$=$R^7$=(i-Pr)$_3$ Si, W=$CH_2$, X=$N_3$] is converted into 20α-4-(3-hydroxypent-3-yl)-1,2,3-triazol-1-ylmethyl-1α,3β-dihydroxy-10-spirocyclopropyl-9,10-secopregna-5(E), 7-diene [Formula (II) —A=(A-7), $R^1$=α-$CH_3$, $R^6$=$R^7$=H, W=$CH_2$, Y=valence bond, Z=4-C($R^4$) ($R^5$).OH where $R^4$=$R^5$=$C_2H_5$];

the compound 20α-azidomethyl-1α,3β-bis-triisopropylsilyloxy-10-spirocyclopropyl-9,10-secopregna-5(Z), 7-diene [Formula (I) —A=(A-6), $R^1$=α-$CH_3$, $R^6$=$R^7$=(i-Pr)$_3$ Si, W=$CH_2$, X=$N_3$] is converted into 20α-4-(3-hydroxypent-3-yl)-1,2,3-triazol-1-ylmethyl-1α,3β-dihydroxy-10-spirocyclopropyl-9,10-secopregna-5(Z), 7-diene [Formula (II) —A=(A-6), $R^1$=α-$CH_3$, $R^6$=$R^7$=H, W=$CH_2$, Y=valence bond, Z=4-C($R^4$) ($R^5$).OH where $R^4$=$R^5$=$C_2H_5$]; and the compound 20β-azidomethyl-1α,3β-bis-t-butyldimethylsilyloxy-19-nor-9,10-secopregna-5,7-diene [Formula (I) —A=(A-8), $R^1$=α-$CH_3$, $R^6$=$R^7$=t-Bu(Me)$_2$ Si, W=$CH_2$, X=$N_3$] is converted into 20β-4-(3-hydroxypent-3-yl)-1,2,3-triazol-1-ylmethyl-1α, 3β-dihydroxy-19-nor-9,10-secopregna-5,7-diene [Formula (II) —A=(A-8), $R^1$=β-$CH_3$, $R^6$=$R^7$=H, W=$CH_2$, Y=valence bond, Z=4-C ($R^4$)($R^5$).OH where $R^4$=$R^5$=$C_2H_5$]

By repeating the procedures of (a)–(c) above using different alkynes the following compounds are obtained:

20α-[4-(3-methyl-3-hydroxybutyl)-1,2,3-triazol-1-ylmethyl]-1α,3β-dihydroxy-9,10-secopregna-5(Z),7,10(19)-triene [Formula (II) —A=(A-2), $R^1$=α-$CH_3$, $R^6$=$R^7$=H, W=$CH_2$, Y=($CH_2$)$_2$, Z=4-C($R^4$)($R^5$).OH where $R^4$=$R^5$=$CH_3$], using 5-methylhex-1-yn-5-ol as alkyne;

20α-[4-(2-methyl-2-hydroxypentyl)-1,2,3-triazol-1-ylmethyl]-1α,3β-dihydroxy-9,10-secopregna-5 (Z),7,10(19)-triene [Formula (II) —A=(A-2), $R^1$=α-$CH_3$, $R^6$=$R^7$=H, W=$CH_2$, Y=$CH_2$, Z=4-C($R^4$)($R^5$).OH where $R^4$=n-$C_3H_7$, $R^5$=$CH_3$], using 4-methylhept-1-yn-4-ol as alkyne;

20α-[4-(4-ethyl-4-hydroxyhexyl)-1,2,3-triazol-1-ylmethyl]-1α,3β-dihydroxy-9,10-secopregna-5(Z),7,10(19)-triene [Formula (II) —A=(A-2), $R^1$=α-$CH_3$, $R^6$=$R^7$=H, W=$CH_2$, Y=$CH_2$, Z=4-C($R^4$)($R^5$).OH where $R^4$=$R^5$=$C_2H_5$], using 6-ethyloct-1-yn-6-ol as alkyne;

20α-[4-(2-hydroxybut-2-yl)-1,2,3-triazol-1-ylmethyl]-1α,3β-dihydroxy-9,10-secopregna-5(Z),7,10(19)-triene [Formula (II) —A=(A-2), $R^1$=α-$CH_3$, $R^6$=$R^7$=H, W=$CH_2$, Y=valence bond, Z=4-C($R^4$) ($R^5$).OH where $R^4$=$C_2H_5$, $R^5$=$CH_3$], using 3-methylpent-1-yn-3-ol as alkyne;

20α-[4-(4-methyl-2-hydroxypent-2-yl)-1,2,3-triazol-1-ylmethyl]-1α,3β-dihydroxy-9,10-secopregna-5 (Z),7,10(19)-triene [Formula (II) —A=(A-2), $R^1$=α-$CH_3$, $R^6$=$R^7$=H, W=$CH_2$, Y=valence bond, Z=4-C($R^4$) ($R^5$).OH where $R^4$=i-$C_4H_9$, $R^5$=$CH_3$] I using 3,5-dimethylhex-1-yn-3-ol as alkyne; and 20α-[4-(2,4-dimethyl-3-hydroxypent-3-yl)-1,2,3-triazol-1-ylmethyl]-1α,3β-dihydroxy-9,10-secopregna-5(Z),7,10(19)-triene [Formula (II) —A=(A-2), $R^1$=α-$CH_3$, $R^6$=$R^7$=H. W=$CH_2$, Y=valence bond, Z=4-C($R^4$) ($R^5$).OH where $R^4$=$R^5$=i-$C_3H_7$], using 2,4-dimethyl-3-ethynylpentan-3-ol as alkyne.

EXAMPLE 15 a) 20α-[4-(2-Hydroxypheneth-2-yl)-1,2,3-triazol-1-ylmethyl]-1α,3β-bis-triisopropylsilyloxy-9,10-secopregna-5(E), 7,10 (19)-triene [Formula (II) —A=(A-3), $R^1$=α-$CH_3$, $R^6$=$R^7$=(i-Pr)$_3$Si, W=$CH_2$, Y=valence bond, Z=4-C($R^4$) ($R^5$).OH where $R^4$=$CH_3$, $R^5$=Ph]

A mixture of the 20α-azide from Example 2 (120 mg), 3-phenylbut-1-yn-3-ol (920 mg) and a few drops of water was heated at 90° for 18 hours, concentrated in vacuo, and the product purified by chromatography to give the title compound (55 mg, major isomer). UV (Et$_2$O) $\lambda_{max}$267, $\lambda_{min}$232 nm; IR (CDCl$_3$) $v_{max}$3610 cm$^{-1}$ (OH); NMR (CDCl$_3$) δ6.8–7.46 (m, triazole H, phenyl-H's), 5.6–6.46 (AB q, 6,7-H's), 4.93 (bs, 19-H's), 3.86–4.4 (m, 1,3-H's), 1.93 (d, $CH_3$ on phenethyl), 0.56 (s, 18-H's).

b) 20α-[4-(2-Hydroxypheneth-2-yl)-1,2,3-triazol-1-ylmethyl]-1α,3β-bis-triisopropylsilyloxy-9,10-secopregna-5(Z) 7,10(19)-triene [Formula (II) —A=(A-2). $R^1$=α-$CH_3$, $R^6$=$R^7$=(i-Pr)$_3$Si, W=$CH_2$, Y=valence bond, Z=4-C($R^4$) ($R^5$).OH where $R^4$=$CH_3$, $R^5$=Ph]

A solution of the 5(E) triene from (a) above (55 mg) was photoisomerised as in Example 1(b) using phenazine (25 mg) in benzene (6 ml). The title compound (33 mg) was isolated by chromatography. UV (Et$_2$O) $\lambda_{max}$261, 262, $\lambda_{min}$228 nm; IR (CDCl$_3$) $v_{max}$3300–3600 cm$^{-1}$ (OH); NMR (CDCl$_3$) δ6.96–7.46 (m, triazole H, Ph-H's), 5.63–6.43 (AD q, 6,7-H's), 4.8, 5.16 (ea s, 19-H's), 3.83–4.5 (bm, 1,3-H's), 1.9 (d, Me on phenethyl), 0.56 (s, 18-H's).

c) 20α-[4-(2-Hydroxypheneth-2-yl)-1,2,3-triazol-1-ylmethyl]-1α,3β-dihydroxy-9,10-secopregna-5(Z),7,10 (19)-triene [Formula (II) —A=(A-2), $R^1$=α-$CH_3$, $R^6$=$R^7$=H, W=$CH_2$, Y=valence bond, Z=4-C($R^4$)($R^5$).OH where $R^4$=$CH_3$, $R^5$=Ph]

The silyl ether from (b) above (33 mg) in THF (0.25 ml) was desilylated as in Example 1(c) using a solution of tetrabutylammonium fluoride in THF (0.25 ml, 1.0M) at room temperature overnight. The title compound (19.2 mg) was isolated by chromatography. A portion was rechromatographed to give 7.8 mg which had UV (EtOH) $\lambda_{max}$262, 263, $\lambda_{min}$228 nm; IR (CDCl$_3$) $v_{max}$3560 cm$^{-1}$ (OH); NMR (CDCl$_3$) δ6.83–7.4 (m, triazole H, Ph-H's), 5.76–6.3 (AB q, 6,7-H's), 4.86, 5.2 (ea s, 19-H's), 3.8–4.43 (bm, 1,3-H's), 2.23 (s, OH), 1.93 (s, $CH_3$ on phenethyl), 0.79 (d, 21 H's), 0.56 (s, 18-H's).

EXAMPLE 16

20α-3-[4-(3-Hydroxypent-3-yl)-1,2,3-triazol-1-yl]propyl-1α,3β-dihydroxy-9,10- secopregna-5(Z) 7,10(19)-triene [Formula (II) —A=(A-2), $R^1$=α-$CH_3$, $R^6$=$R^7$=H, W=($CH_2$)$_3$, Y=valence bond, Z=4-C($R^4$)($R^5$).OH] where $R^4$=$R^5$=$C_2H_5$]

A mixture of the 1α,3β-dihydroxy-5(Z)-20-azidopropyl compound from Example 1(c) (10 mg), 3-ethylpent-1-yn-3-ol (200 mg) and a few drops of water was heated at 50° for 7 hours, then at 70° for 34 hours, concentrated in vacuo, and the product was purified by chromatography to give the title compound (5.2 mg). UV (EtOH) $\lambda_{max}$263, $\lambda_{min}$232–232 nm; IR (CDCl$_3$) $\nu_{max}$3560 cm$^{-1}$ (OH); NMR (CDCl$_3$) $\delta$7.13 (m, triazole H), 5.73–6.4 (AB q, 6,7-H's), 4.76, 5.06 (ea s, 19-H's), 3.86–4.33 (m, 1,3-H's), 1.63–1.83 (m, OH, C$\underline{H}_2$CH$_3$), 0.6–0.83 (m, 21-H's, $\underline{C}H_3$CH$_2$), 0.43 (s, 18-H's).

We claim:

1. A compound of formula (I)

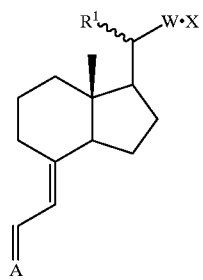

(I)

where R$^1$ represents a methyl group having α- or β- configuration or a dimethyl, methylene or spirocyclopropyl group; W represents a valence bond or a C$_{1-5}$ alkylene group; X represents azide; and A= represents a group selected from the group consisting of

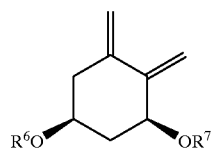

(A-2)

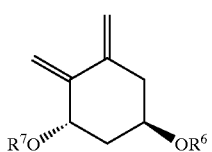

(A-3)

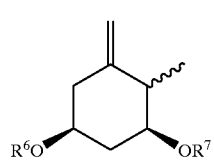

(A-4)

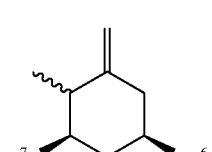

(A-5)

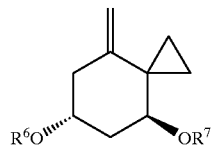

(A-6)

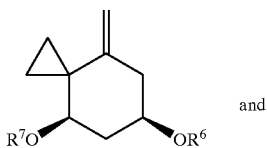

and (A-7)

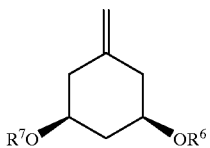

(A-8)

where R$^6$ and R$^7$, which may be the same or different, each represent a hydrogen atom or an O-protecting group which is an etherifying group which is a tri(C$_{1-6}$ alkyl)silyl, tri-(C$_{6-12}$ aryl)silyl or mixed C$_{1-6}$ alkyl-C$_{6-12}$ arylsilyl group, a C$_{1-6}$ alkyl group optionally interrupted by an oxygen atom or a tetrahydropyranyl group or is an esterifying group which is a C$_{1-6}$alkanoyl group, an aroyl group containing 7–15 carbon atoms, a C$_{1-6}$ alkane sulphonyl group optionally substituted with a halogen atom or a p-toluene sulphonyl group.

2. A compound as claimed in claim 1 wherein W represents a valence bond, a methylene, ethylene or trimethylene group.

3. A compound as claimed in claim 1 wherein R$^6$ and R$^7$ are hydrogen atoms.

4. A compound as claimed in claim 1 wherein A= represents one of the groups selected from the group consisting of

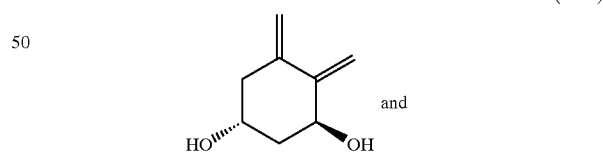

(A-2a)

and

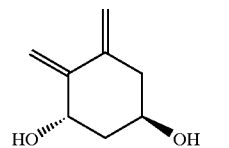

(A-3a)

5. The compound of claim 1 which is 20α-(3-azidopropyl)-1α,3β-dihydroxy-9,10-secopregna-5(Z),7,10 (19)-triene.

6. The compound of claim 1 which is 20α-azido-1α,3β-dihydroxy-9,10-secopregna-5(Z),7,10(19)-triene.

7. A process for the preparation of a compound of formula (I) as defined in claim 1 which comprises one or more of:
  A) isomerising a 5,6-trans isomer of formula (I) to a corresponding 5,6-cis isomer, followed if necessary and/or desired by removal of any O-protecting groups;
  B) hydroxylating a 1-unsubstituted-5,6-trans analogue of a compound of formula (I) to prepare a 5,6-trans isomer of formula (I), followed if necessary and/or desired by isomerisation and/or removal of any O-protecting group;
  C) reacting a compound containing a precursor for the desired 17-position side chain in one or more stages and with one or more reactants serving to form the desired side chain, followed if necessary and/or desired by isomerisation and/or removal of any O-protecting groups; and
  D) reacting a compound of formula (I) to modify the substitution pattern about the A= group, followed if necessary and/or desired by isomerisation and/or removal of any O-protecting groups.

8. A process as claimed in claim 7 wherein a compound of formula (III)

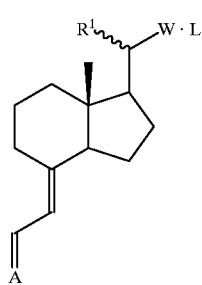

(III)

(where L represents a leaving group) or a precursor therefor is reacted with a source of azide ions.

* * * * *